US008846872B2

(12) United States Patent
Kertesz et al.

(10) Patent No.: US 8,846,872 B2
(45) Date of Patent: Sep. 30, 2014

(54) MONOCLONAL ANTIBODIES AND DIAGNOSTIC USES THEREOF

(75) Inventors: Nathalie Kertesz, Agoura Hills, CA (US); Sutao Zhu, Alhambra, CA (US); Chih-Sheng Chiang, Chatsworth, CA (US)

(73) Assignee: MannKind Corporation, Valencia, CA (US)

( * ) Notice: Subject to any disclaimer, the term of this patent is extended or adjusted under 35 U.S.C. 154(b) by 153 days.

(21) Appl. No.: 13/510,901

(22) PCT Filed: Nov. 18, 2010

(86) PCT No.: PCT/US2010/003012
§ 371 (c)(1),
(2), (4) Date: Oct. 17, 2012

(87) PCT Pub. No.: WO2011/062634
PCT Pub. Date: May 26, 2011

(65) Prior Publication Data
US 2013/0029359 A1    Jan. 31, 2013

Related U.S. Application Data

(60) Provisional application No. 61/262,538, filed on Nov. 18, 2009.

(51) Int. Cl.
*C07K 16/30* (2006.01)
*G01N 33/574* (2006.01)
*C07K 14/47* (2006.01)

(52) U.S. Cl.
CPC ...... *G01N 33/57484* (2013.01); *G01N 33/5743* (2013.01); *C07K 14/47* (2013.01); *C07K 16/3053* (2013.01); *C07K 2317/34* (2013.01)
USPC .................. 530/388.8; 530/387.3; 530/387.7; 530/387.9; 435/7.1; 435/7.23; 435/330; 435/331; 536/23.53

(58) Field of Classification Search
CPC .............. C07K 16/30; C07K 16/3053; C07K 16/3069; C07K 16/32; C07K 16/40; C07K 2317/34; G01N 33/5017; G01N 33/53; G01N 33/574; G01N 33/5743; G01N 33/57484
See application file for complete search history.

(56) References Cited

U.S. PATENT DOCUMENTS

| | | | |
|---|---|---|---|
| 5,830,753 | A | 11/1998 | Coulie |
| 6,017,716 | A | 1/2000 | Pfreundschuh |
| 6,025,191 | A | 2/2000 | Pfreundschuh |
| 6,548,064 | B1 | 4/2003 | Tureci |
| 6,861,234 | B1 | 3/2005 | Simard |
| 7,511,119 | B2 | 3/2009 | Liu |
| 8,202,841 | B2 | 6/2012 | Liu |
| 2003/0186355 | A1 | 10/2003 | Ossendorp |
| 2003/0220239 | A1 | 11/2003 | Simard |
| 2004/0063101 | A1 | 4/2004 | Scanlan |
| 2004/0253235 | A1 | 12/2004 | Durda |
| 2006/0063913 | A1 | 3/2006 | Liu |
| 2006/0159689 | A1 | 7/2006 | Chiang |
| 2009/0175880 | A1 | 7/2009 | Keler |

FOREIGN PATENT DOCUMENTS

| | | |
|---|---|---|
| WO | WO 2006/138562 | 12/2006 |
| WO | WO 2008/110372 A1 | 9/2008 |
| WO | WO 2008/118017 | 10/2008 |

OTHER PUBLICATIONS

Proto-Siqueira et al., Leukemia Res 2006; 30:1333-39.*
Valmori et al. Clin Cancer Res 2006; 12:398-404.*
Ayyoub, M. et al., "Proteasome-Assisted Identification of a SSX-2-Derived Epitope recognized by Tumor-Reactive CTL Infiltrating Metastatic Melanoma," *J Immunol.*, 2002, 168(4): 1717-1722.
Ayyoub, M. et al., "Tumor-reactive, SSX-2-specific CD8+ T Cells Are Selectively Expanded during Immune Responses to Antigen-expressing Tumors in Melanoma Patients," *Cancer Res.*, 2003, 63(17): 5601-5606.
Bustin, S.A., "Absolute quantification of mRNA using real-time reverse transcription polymerase chain reaction assays," *J. Mol. Endocrin.*, 2000, 25:169-193.
Epping, M. et al., "The Human Tumor Antigen PRAME Is a Dominant Repressor of Retinoic Acid Receptor Signaling," *Cell*, 2005, 122(6):835-847.
Epping, M. et al., "A Causal Role for the Human Tumor Antigen Preferentially Expressed Antigen of Melanoma in Cancer," *Cancer Res.*, 2006, 66(22): 10639-10642.
Gure, A.O. et al., "SSX: A Multigene Family with Several Members Transcribed in Normal Testis and Human Cancer," *Int. J. Cancer*, 1997, 72:965-971.
Köhler, G. and Milstein, C., "Derivation of Specific Antibody-Producing Tissue Culture and Tumor Lines by Cell Fusion," *Eur. J. Immunol.*, 1976, 6:511-519.
Matsushita, M. et al., "Quantitative monitoring of the PRAME gene for the detection of minimal residual disease in leukaemia," *Br. J Haematol.*, 2001, 112(4):916-926.
Matsushita, M. et al., "Quantitative analysis of PRAME for detection of minimal residual disease in acute myeloblastic leukemia," *Methods Mol. Med.*, 2004, 97:267-275.
Proto-Siqueira, R. et al., "The expression of PRAME in chronic lymphoproliferative disorders," *Leukaemia Res.*, 2003, 27(5):393-396.

(Continued)

*Primary Examiner* — Sheela J Huff
*Assistant Examiner* — Jessica H Roark
(74) *Attorney, Agent, or Firm* — Davis Wright Tremaine LLP

(57) ABSTRACT

The disclosure relates to antibodies to the preferentially expressed antigen in melanoma (PRAME), and the synovial sarcoma X breakpoint 2 (SSX-2) antigens, methods of use, and diagnostic kits thereof. In exemplary embodiments, the disclosure relates to monoclonal antibodies to specific epitopes of the PRAME and SSX-2 antigens and methods of using such antibodies.

15 Claims, 10 Drawing Sheets

(56) References Cited

OTHER PUBLICATIONS

Tajeddine, N. et al., "Tumor-Associated Antigen Preferentially Expressed Antigen of Melanoma (PRAME) Induces Caspase-Independent Cell Death in vitro and Reduces Tuorigenicity in vivo," *Cancer Res.*, 2005, 65(16):7348-7355.

Taylor, B. et al., "SSX Cancer Testis Antigens are Expressed in Most Multiple Myeloma Patients: Co-Expression of SSX1, 2, 4, and 5 Correlates With Adverse Prognosis and High Frequencies of SSX-Positive PCs," *J. Immunotherapy*, 2005, 28(6):564-575.

van Baren et al., "PRAME, a gene encoding an antigen recognized on a human melanoma by cytolytic T cells, is expressed in acute leukaemia cells," *Br J Haematol.*, 1998, 102(5):1376-9.

Wagner, C. et al., "Identification of an HLA-A*02 restricted immunogenic peptide derived from the cancer testis antigen HOM-MEL-40/SSX2," *Cancer Immunity*, 2003, 3:18.

PCT International Search Report in corresponding International application No. PCT/US2010/003012, published Oct. 21, 2011.

Ikeda, H et al., "Characterization of an antigen that is recognized on a melanoma showing partial HLA loss by CTL expressing an NK inhibitory receptor," *Immunity*, 1997, 6(2):199-208.

Kessler, JH et al., "Efficient Identification of Novel HLA-A*0201-presented Cytotoxic T Lymphocyte Epitopes in the Widely Expressed Tumor Antigen PRAME by Proteasome-mediated Digestion Analysis," *J. Exp. Med.*, 2001, 193:73-88.

Proto-Siqueira, R et al.," PRAME is a membrane and cytoplasmic protein aberrantly expressed in chronic lymphocytic leukemia and mantle cell lymphoma," *Leukemia Research*, 2006, 30(2006):1333-1339.

Office Action in related Chinese Patent Application No. 201080060979.1, dated Sep. 13, 2013, 2 pages.

* cited by examiner

FIGURE 2

Immunohistochemical Analysis Raw Data Sheet

*(a) Sensitivity Worksheet*

| GENERAL SPECIMEN INFORMATION | | | TEST ARTICLE STAINING OF DISTINCTIVE TISSUE ELEMENTS | | | | B. TEST ARTICLE STAINING OF OTHER CELL TYPES | | | | | |
|---|---|---|---|---|---|---|---|---|---|---|---|---|
| Specimen ID # | Histologic Review | Isotype Control Background | % cells staining at each intensity | | | | Normal | Endo- thelium | Smooth Muscle | Fibro- blast | Stroma | Inflam. Cells | Nerve |
| | | | 3+ | 2+ | 1+ | 0 | | | | | | | |
| ITME02883B | Melanoma | 0 | 30 N,C | 50 N,C | 20 N,C | 0 | NS | 1+, 2+ | NS | 2+ | ± | 2+, Sc | NS |
| ITME0006-192-01127-5 | Melanoma | 0 | 5 N,C | 50 N,C | 45 N,C | 0 | 2+ N | 1+ | NS | 1+ | 0 | 1+, 2+ Sc | NS |
| ITME0008-192-00537-9 | c/w Melanoma | 0 | 0 | 0 | 0 | 100 | NS | ± | 1+ | 1+ | 0 | ± | NS |
| ITME0007-192-00943-8 | c/w Melanoma | 0 | 30 N,C | 60 N,C | 10 N,C | 0 | NS | 2+ | NS | 2+ | 0, ± | 2+, Sc | NS |
| ITME0009-192-00229-1 | c/w Melanoma | 0 | 0 | 20 N,C | 70 N,C | 10 | NS | 1+ | NS | 1+, 2+ | 0 | 1+, 2+ Sc | NS |
| ITME0009-192-01137-8 | Melanoma | 0 | 0 | 10 N,C | 50 N,C | 40 | 1+, N | 1+ | NS | 1+ | 0 | 1+, Sc | NS |
| ITME0012-192-08893-3 | Melanoma | 0 | 0 | 20 N,C | 80 N | 0 | 2+ | 1+ | NS | 1+, 2+ | 0 | 1+, 2+ SC | NS |
| ITME0012-192-01919-7 | Melanoma | 0, ± | 20 N,C | 70 N,C | 10 N,C | 0 | 3+ | 2+ | NS | 2+ | 0 | 2+, SC | NS |

FIGURE 2 (cont'd)

| GENERAL SPECIMEN INFORMATION | | | TEST ARTICLE STAINING OF DISTINCTIVE TISSUE ELEMENTS | | | | C. TEST ARTICLE STAINING OF OTHER CELL TYPES | | | | | |
|---|---|---|---|---|---|---|---|---|---|---|---|---|
| Specimen ID # | | Histologic Review | Isotype Control Background | % cells staining at each intensity | | | | Normal | Endo-thelium | Smooth Muscle | Fibro-blast | Stroma | Inflam. Cells | Nerve |
| | | | | 3+ | 2+ | 1+ | 0 | | | | | | | |
| ITME0104-292-00991-2A | Melanoma | Melanoma | 0 | 10 N, C | 30 N, C | 50 N, C | 10 | 1+, 2+ | 1+, 2+ | NS | 2+ | 0, ± | 2+, Sc | NS |
| ITME0104-292-01045-6 | Melanoma | Melanoma | 0 | 25 N, C | 60 N, C | 15 N | 0 | 3+ | 1+, 2+ | NS | 2+ | ± | 2+, Sc | NS |
| ITME0104-292-01071-2 | Melanoma | Melanoma | 0 | 40 N, C | 40 N, C | 20 N, C | 0 | 3+ | 1+, 2+ | ± | 2+ | 0 | 2+, Sc | NS |
| ITME0104-303-01265-1 | Melanoma | Melanoma | 0, ± | 0 | 0 | 10 N | 90 | NS | ± | NS | ± | 0 | ± | NS |
| ITME0104-303-01396-2 | Melanoma¹ | Melanoma | 0 | 20 N, C | 40 N, C | 30 N | 10 | 3+ | 2+ | NS | 2+ | ± | 2+, Sc | NS |
| ITME0104-303-01713-8 | Melanoma | Melanoma | 0 | 80 N, C | 20 N, C | 0 | 0 | 3+ | 2+ | 2+ | 2+ | ± | 2+, 3+ Sc | NS |
| ITME0104-303-01837-3 | Melanoma | Melanoma | 0 | 30 N, C | 30 N, C | 40 N | 0 | 2+, 3+ | 2+ | NS | 2+ | ± | 2+, Sc | NS |
| ITME0105-292-01439-2 | Melanoma | c/w Melanoma | 0 | 30 N, C | 50 N, C | 20 N | 0 | 2+, 3+ | 2+ | NS | 2+ | 0, ± | 2+ Sc | NS |
| ITME0105-303-00874-8 | Melanoma | Melanoma | 0 | 20 N, C | 50 N, C | 30 | 0 | 2+, 3+ | 2+ | NS | 2+ | ± | 2+ Sc | NS |
| ITME0105-303-00914-5 | Melanoma | Melanoma | 0 | 30 N, C | 40 N, C | 30 N | 0 | 3+ | 2+ | NS | 2+ | ± | 2+ Sc | NS |
| ITME0105-303-02581-2 | Melanoma | Melanoma | 0 | 10 N, C | 30 N, C | 50 N | 10 | 2+, 3+ | 2+ | NS | 2+ | ± | 2+ Sc | 2+ |
| ITME0109-192-00674-1 | Melanoma | Melanoma | 0 | 0 | 30 N, C | 50 N | 20 | 1+ | 1+ | NS | 1+ | ± | 1+ Sc | NS |

FIGURE 2 (cont'd)

± = Equivocal Results
NA = Not Applicable
NS = Not Seen
Ap = Apical Staining
B = Basal Layer Staining
C = Cytoplasmic Staining
F = Focally Positive
La = Luminal Accentuation H = Heterogeneous Staining
I = Inflammatory Cells
M = Membrane Staining
N = Nuclear Staining
P = Perineural Staining
S = Stroma
Sc = Scattered
c/w = Consistent With

COMMENTS/NOTES:
1 Sebaceous glands are staining 3+.

MONOCLONAL ANTIBODIES AND DIAGNOSTIC USES THEREOF

CROSS-REFERENCE TO RELATED APPLICATIONS

The present application is a U.S. National Stage entry under 35 U.S.C. 0371 of International Application No. PCT/US2010/003012, filed on Nov. 18, 2010, designating the United States of America and published in English on May 26, 2011, which in turn claims priority to U.S. Provisional Application No. 61/262,538, filed on Nov. 18, 2009, each of which is herby incorporated by reference in its entirety.

FIELD OF THE INVENTION

The disclosure relates to antibodies to the preferentially expressed antigen in melanoma (PRAME), and the synovial sarcoma X breakpoint 2 (SSX-2) antigens, methods of use, and diagnostic kits thereof. In particular, the disclosure relates to monoclonal antibodies to specific epitopes of the PRAME and SSX-2 antigens and methods of using such antibodies.

BACKGROUND

The American Cancer Society has estimated that almost 1.5 million new cases of cancer will be diagnosed this year. This includes carcinoma in situ of the urinary bladder but excludes those of other sites such as basal and squamous cell skin cancers. Approximately one out of every two American men and one out of every three American women will have some type of cancer at some point during their lifetime.

One means of targeting cancer is by early screening and detection as well as diagnosis at an early disease stage which allow for treatment and prevention of later stage disease. A number of cancers when detected, screened or diagnosed early, can be more successfully treated. Although a number of therapeutic remedies exist, a continuing need remains for additional tools to better aid in preventing, screening, diagnosing and targeting a cancer with the appropriate therapeutic regimen. Such tools, for example, involve tumor-associated antigens of the cancer testis family against which both humoral and cellular immune responses have been observed in patients with different types of cancers.

Clinical trials on the use of tumor-associated antigen-specific vaccines are underway and show promising preliminary results. For a vaccine which is used to treat tumors expressing the targeted tumor-associated antigens, it can be useful to determine which TAA are expressed by a patient's tumor. Detecting the level of expression of specific TAAs in tumor tissues provide a convenient method to obtain the expression profile of TAAs in a patient's tumor. Hence diagnostic tools that can complement such cancer therapies are of value.

SUMMARY OF THE DISCLOSURE

Some embodiments of the disclosure relate to antibodies that bind specifically to an epitope of the PRAME tumor-associated antigen. Some embodiments of the disclosure relate to isolated antibodies that bind specifically to an epitope of the SSX-2 tumor-associated antigen.

Some embodiments relate to an anti-PRAME antibody, or one or more antigen binding fragments thereof, that binds specifically to an epitope comprising amino acid residues 123-132 of the PRAME antigen (SEQ ID NO:1). Some embodiments relate to an anti-PRAME antibody, or one or more antigen binding fragments thereof, that binds specifically to an epitope comprising amino acid residues 276 to 286 of the PRAME antigen (SEQ ID NO:2).

Some embodiments relate to an anti-SSX-2 antibody, or one or more antigen binding fragments thereof, that binds specifically to an epitope comprising amino acid residues 41-49 of the SSX-2 antigen (SEQ ID NO:3). Some embodiments relate to an anti-SSX-2 antibody, or one or more antigen binding fragments thereof, that binds specifically to an epitope comprising amino acid residues 120 to 128 of the SSX-2 antigen (SEQ ID NO:4).

In some embodiments the antibodies, or polypeptides comprising an antigen binding portion thereof, disclosed herein are monoclonal antibodies. In some embodiments the antibodies disclosed herein are murine antibodies. In some embodiments, the antibodies disclosed herein are humanized antibodies. In some embodiments, the antibodies disclosed herein are chimeric antibodies. In some embodiments the antibodies disclosed herein are human antibodies.

In some embodiments, the anti-PRAME antibody, or polypeptide comprising an antigen binding portion thereof, binds specifically to SEQ ID NO:1. In some embodiments, the anti-PRAME antibody, or polypeptide comprising an antigen binding portion thereof, binds specifically to SEQ ID NO:2. In some embodiments, the anti-PRAME antibody is a murine monoclonal antibody. In some embodiments, the anti-PRAME antibody is a humanized antibody. In some embodiments, the anti-PRAME antibody is a chimeric antibody. In some embodiments, the anti-PRAME antibody is a human antibody.

In some embodiments, the anti-SSX-2 antibody, or polypeptide comprising an antigen binding portion thereof, binds specifically to SEQ ID NO:3. In some embodiments, the anti-SSX-2 antibody, or polypeptide comprising an antigen binding portion thereof, binds specifically to SEQ ID NO:4. In some embodiments, the anti-SSX-2 antibody is a murine monoclonal antibody. In some embodiments, the anti-SSX-2 antibody is a humanized antibody. In some embodiments, the anti-SSX-2 antibody is a chimeric antibody. In some embodiments, the anti-SSX-2 antibody is a human antibody.

In some embodiments the antibodies disclosed herein are linked to a label. In one some embodiments, the label is a detectable marker or a detectable agent. In some embodiments, the label can bind to/or be bound to by another molecule that is a detectable marker. In some embodiments, the label can include a molecule that is conjugated or linked to a detectable marker.

In some embodiments, the method is a method for detecting expression of tumor associated antigen PRAME. In some embodiments, the method is a method for detecting expression of tumor associated antigen SSX-2. In some embodiments, the method is a method for detecting expression of tumor associated antigens PRAME and SSX-2. Thus, some embodiments relate to a method of detecting expression of tumor-associated antigen PRAME, SSX-2, or both, in a subject. Some embodiments relate to a method of detecting expression of tumor associated antigen PRAME, SSX-2, or both in a biological sample. The method includes contacting the biological sample (for example in cells or tissue obtained in the sample) with an antibody described herein and detecting antibody bound to antigen contained in the sample, thereby detecting expression of the tumor associated antigen. In some embodiments, the method of includes obtaining the biological sample from a subject, for instance from a mammal, such as from a human.

In some embodiments, the subject has cancer. In some embodiments, the cancer can be, but is not limited to, melanoma, kidney, breast, pancreas, prostate, colorectal, liver, ovarian, non small cell lung cancer, glioblastoma, ocular melanoma, hormone sensitive and hormone refractory prostate cancer, renal cell carcinoma, esophageal, endometrial cancer, uterine cancer, lymphoma, soft tissue sarcoma, multiple myeloma, gallbladder cancer, thyroid, mesothelioma, and the like. In some embodiments, the biological sample can be, but is not limited to, a biopsy specimen, a tissue (such as tumor tissue), a cell (such as a cancer or tumor cell), blood, ascites, pleural fluid, a soluble protein, and the like. In some embodiments, expression of PRAME, SSX-2, or both is detected by immunofluorescence microscopy, immunocytochemistry, immunopreciptation, immunohistochemistry, ELISA (Enzyme-linked immunosorbent assay), FACS (Fluorescence activated cell sorter) analysis and the like.

Some embodiments relate to a hybridoma that produces a monoclonal antibody as disclosed herein. Accordingly, some embodiments relate to a hybridoma that produces a monoclonal antibody that binds specifically to a peptide having the sequence of SEQ ID NO:1, SEQ ID NO:2, SEQ ID NO:3 or SEQ ID NO:4.

Some embodiments of the disclosure relate to a diagnostic kit including an antibody disclosed herein. For example, some embodiments relate to a diagnostic kit comprising an anti-PRAME antibody, or one or more antigen-binding fragments thereof, that binds specifically to an epitope comprising amino acid residues 123-132 of the PRAME antigen (SEQ ID NO:1). Some embodiments relate to a diagnostic kit containing an anti-PRAME antibody, or one or more antigen-binding fragments thereof, that binds specifically to an epitope comprising amino acid residues 276 to 286 of the PRAME antigen (SEQ ID NO:2). Some embodiments of the disclosure relate to a diagnostic kit comprising an anti-SSX-2 antibody, or one or more antigen binding fragments thereof, that binds specifically to an epitope comprising amino acid residues 41-49 of the SSX-2 antigen (SEQ ID NO:3). Some embodiments relate to a diagnostic kit comprising an anti-SSX-2 antibody, or one or more antigen binding fragments thereof, that binds specifically to an epitope comprising amino acid residues 120 to 128 of the SSX-2 antigen (SEQ ID NO:4).

Some embodiments of the disclosure relate to a nucleic acid means or molecule that operably encodes an antibody, or antigen binding fragment thereof, disclosed herein. The nucleic acid means or molecule can include a plasmid. In some embodiments, the anti-PRAME antibody, or one or more antigen binding fragments thereof, specifically binds an epitope comprising amino acid residues 123-132 of the PRAME antigen (SEQ ID NO:1), or a portion of the epitope. In some embodiments, the anti-PRAME antibody, or one or more antigen binding fragments, binds specifically to an epitope comprising amino acid residues 276 to 286 of the PRAME antigen (SEQ ID NO:2), or a portion of the epitope.

Some embodiments of the disclosure relate to a nucleic acid means or molecule operably encodes an antibody, or antigen binding fragment thereof, disclosed herein. The nucleic acid means or molecule can include a plasmid. In some embodiments, the anti-SSX-2 antibody, or one or more antigen binding fragments thereof, binds specifically to an epitope comprising amino acid residues 41-49 of the SSX-2 antigen (SEQ ID NO:3), or a portion of the epitope. In some embodiments, the anti-SSX-2 antibody, or one or more antigen binding fragments thereof, binds specifically to an epitope comprising amino acid residues 120 to 128 of the SSX-2 antigen (SEQ ID NO:4), or a portion of the epitope.

DETAILED DESCRIPTION

Definitions

Figure 1:
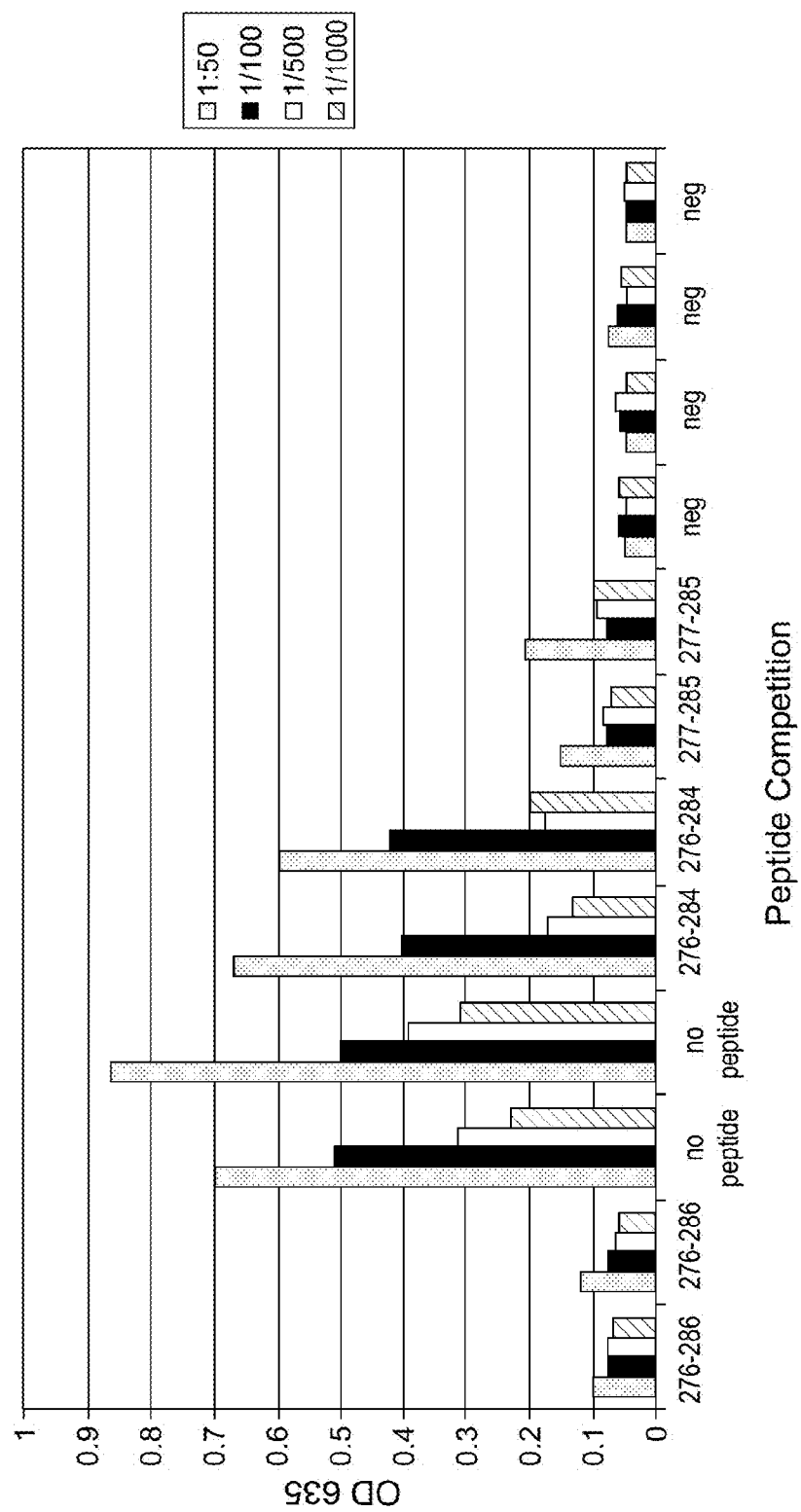
FIG. 1. Depicts minimal epitope mapping of $PRAME_{276-286}$ epitope. For each type of peptide or no peptide or negative control, serially diluted 1:50 (the first column), 1:100 (the second column), 1:500 (the third column) and 1:1000 (the fourth column) were analyzed.
Figure 1:
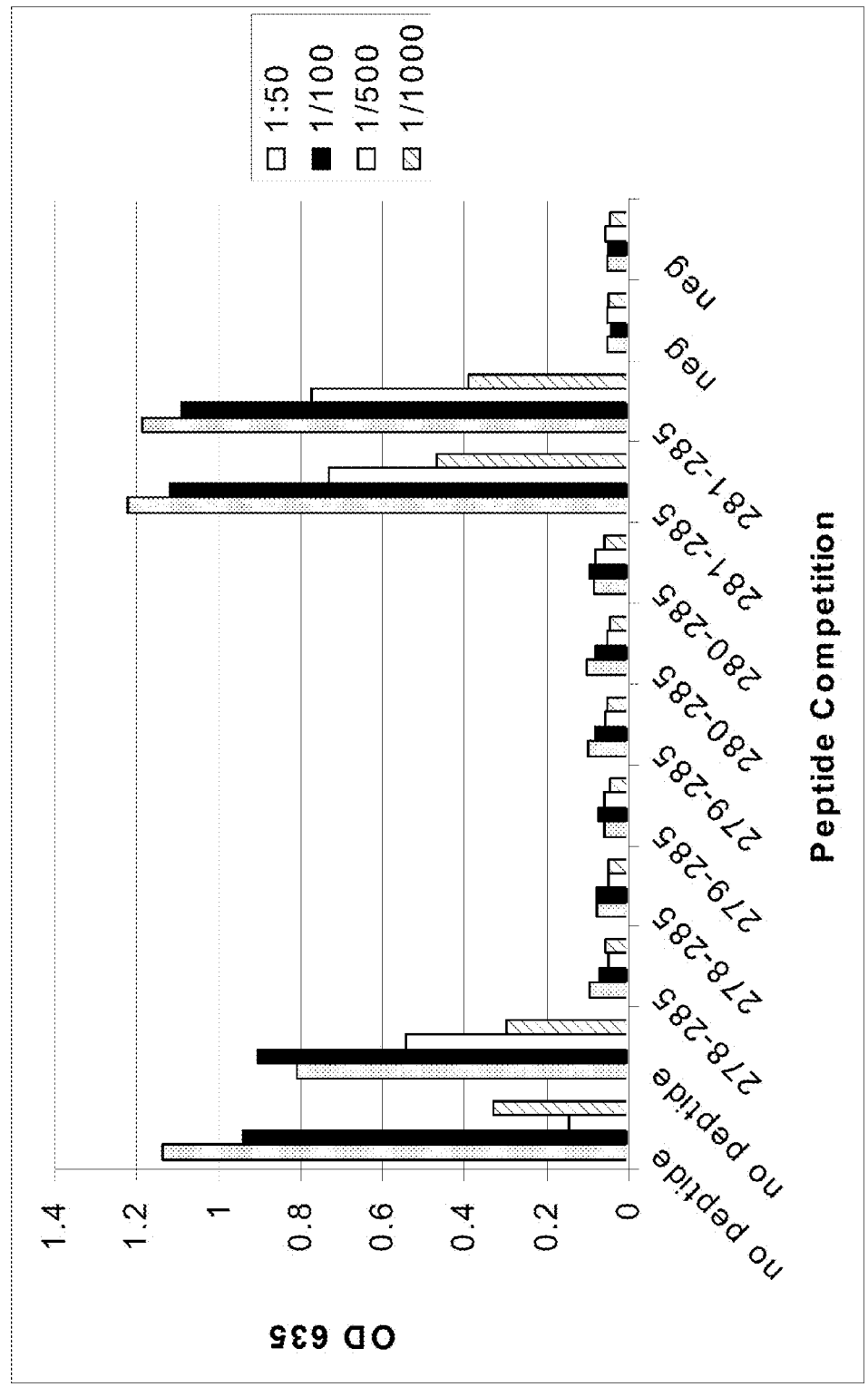

Unless otherwise clear from the context of the use of a term herein, the following listed terms shall generally have the indicated meanings for purposes of this description.

The terms "antibody" or "antibodies" as used herein are art recognized terms. and are understood to refer to molecules or active fragments of molecules, particularly immunoglobulin molecules and immunologically active portions of immunoglobulin molecules, that bind to antigens, i.e. molecules that contain a binding site that immunospecifically binds an anti-antigen. In some embodiments, the definition includes antiserum or immune serum.

The term "monoclonal antibody" is a term well recognized in the art and refers to an antibody that is from a single clone. Monoclonal antibodies are typically made by fusing a normally short-lived, antibody-producing B cell to a fast-growing cell, such as, a cancer cell (sometimes referred to as an "immortal" cell). The resulting hybrid cell or hybridoma, multiplies rapidly, creating a clone that produces large quantities of the antibody.

As used herein, the term "isolated," when used as a modifier of an composition described herein (e.g., antibodies, antigen binding portion, nucleic acids encoding same, cells, vectors, etc.), means that the compositions are made by the hand of man or are separated from their naturally occurring in vivo environment. The term "isolated" refers to material (e.g., a biological molecule) which is substantially or essentially free from components which normally accompany it as found in its native state.

The term "hybridoma" is art recognized and is understood by those of ordinary skill in the art to refer to a cell produced by the fusion of an antibody-producing cell and an immortal cell, e.g., a multiple myeloma cell. This hybrid cell is capable of producing a continuous supply of antibody.

The term "epitope" refers to a site on an antigen recognized by an antibody or an antigen receptor.

The term "binds specifically" as used herein refers to the act of an antibody binding to the relevant epitope and is intended to exclude low-level, non-specific binding that may occur between random proteins. "Binds specifically" as used herein is not intended and does not imply that the antibody will not bind to any epitope other than the epitopes disclosed herein.

The terms "detecting" or "detected" as used herein refer to using known techniques for detection of biological molecules such as immunochemical or histological methods and refer to qualitatively or quantitatively determining the presence, prevalence, or concentration of the biomolecule under investigation.

As used herein, the terms "label" or "labeled" refers to incorporation of another molecule in the antibody. In one some embodiments, the incorporated molecule (i.e. the label) is a detectable marker or a detectable agent. In one some embodiments, the incorporated molecule is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In some embodiments, the incorporated molecule (i.e. the label) can bind to/or be bound to by another molecule that is a detectable marker or is conjugated or linked to a detectable marker. In another embodiment, the incorporated molecule can be therapeutic, e.g., a drug conjugate or toxin. Various methods of labeling polypeptides and glycoproteins are known in the art and can be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, beta-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

As used herein, the term "operably encoding" refers a plasmid which when present in a host cell, such as a bacterial, yeast, insect or mammalian cell, has a cistron that can be transcribed into mRNA and translated into protein, or protein fragment.

The instant disclosure relates to the generation of antibodies specifically directed against tumor-associated antigens. Such antibodies allow for the detection of these antigens in a variety of cancers. In some embodiments, such antibodies can be used in assessing, applying, administering or determining the appropriate immunotherapeutic treatment for patients having a particular cancer.

In some embodiments, the disclosure relates to an isolated antibody, or antigen-binding fragment thereof, directed against PRAME antigen that binds an epitope comprising or consisting essentially of an amino acid sequence of SEQ ID NO:1 or SEQ ID NO:2. In some embodiments, the disclosure relate to an isolated antibody, or antigen-binding fragment thereof, directed against SSX-2 antigen that binds an epitope comprising or consisting essentially of an amino acid sequence of SEQ ID NO:3 or SEQ ID NO:4. In some embodiments the "antigen binding fragment thereof" exists as a complete polypeptide, while in other embodiments it is incorporated into a longer polypeptide molecule.

In some embodiments, the disclosure provides a method of detecting expression of tumor-associated antigen PRAME, SSX-2, or both, in a subject having cancer, comprising contacting a biological sample from the subject with an antibody directed against SSX-2 or PRAME antigen as described herein; and detecting antibody bound to the sample; thereby detecting the expression of the tumor associated antigen.

In embodiments disclosed herein, PRAME monoclonal antibodies disclosed have specificity for the PRAME protein. In some embodiments, the $PRAME_{276-286}$ and $PRAME_{123-132}$ monoclonal antibodies are each specific only to the PRAME protein in that they each bind to a unique peptide on PRAME as shown by immunohistochemical analysis, described herein. In exemplary embodiments a BLAST protein search (an algorithm for comparing amino-acid sequences of different proteins, i.e. amino acid residues to 276-286 (SEQ ID NO:2) or 123-132 (SEQ ID NO:1) of the PRAME protein were compared with a library or database of amino acid sequences) is utilized in assessing specificity of an antibody raised against the particular epitopes. Such algorithms and uses thereof are known in the art.

As described in the Examples, specificity of the $PRAME_{276-286}$ monoclonal antibody to the PRAME protein was assessed by determining the minimal region of the $PRAME_{276-286}$ epitope recognized by the monoclonal antibody. Short peptide sequences from overlapping segments of $PRAME_{276-286}$ (SEQ ID NO:2) were analyzed for competitive binding with the $PRAME_{276-286}$ immunogen. In some embodiments, the minimal region of $PRAME_{276-286}$ recognized by the $PRAME_{276-286}$ monoclonal antibody was 280-285. The specificity of the $PRAME_{276-286}$ and $PRAME_{123-132}$ monoclonal antibodies as analyzed by BLAST protein search, indicated that no other known human protein was cross-reactive with the amino acid sequence of 276-286 (SEQ ID NO:2), and/or the minimal region corresponding to amino acid sequence 280-285, or 123-132 (SEQ ID NO:1) of the PRAME protein. In some embodiments, specificity of the $PRAME_{276-286}$ and $PRAME_{123-132}$ monoclonal antibodies was further indicated by IHC staining of a variety of tumor tissues in a peptide competition assay, (see Example 7). In the presence of an excess amount of PRAME peptide, (such as at least 2-fold, or at least 4-fold, or at least 6-fold, or at least 8-fold, or at least 10-fold, but not limited to such), the $PRAME_{276-286}$ and $PRAME_{123-132}$ monoclonal antibodies exhibit competitive binding. The data supports the advantageous specificity of the PRAME antibodies disclosed in that they lack cross-reactivity with non-target antigens.

The $PRAME_{276-285}$ antibody was validated for use in immunohistochemical analysis of tissue. The antibody showed good sensitivity and specificity, thus validating the antibody for use, for example, in immunohistochemical assays, such as assays aimed at diagnosis of cancer or analysis of protein expression in cancerous cells (see Example 6). The specificity of the antibodies is relevant in relation not only to immunohistochemical analysis but also to a broad range of other analytical techniques in which the antibody is employed in detection of the antigen in a sample. For instance, if the antibody is used in an analysis of protein expression in a particular cell or tissue, such as a cancerous cell or a tumor, the high specificity of the antibody will minimize the number of false positive results, thus leading to a more reliable analysis. In embodiments herein, the PRAME monoclonal antibodies of the disclosure that recognize $PRAME_{276-286}$ epitope or the $PRAME_{123-132}$ epitope, have utility as diagnostic tools in that each can complement cancer therapies that target the PRAME tumor associated antigen. In some embodiments, the PRAME monoclonal antibodies of the disclosure can be utilized in standard assays such as, ELISA, FACS analysis, immunohistochemistry, immunocytology and immunohistology assays, immunoprecipitation and Western blotting to detect the expression of PRAME antigen in tumor tissues or cancerous cells.

In some embodiments the $SSX-2_{41-49}$ and $SSX-2_{120-128}$ monoclonal antibody are specific only to the SSX-2 protein in that each binds to a unique peptide on SSX-2 as shown by immunohistochemical analysis, described herein. Specificity of the antibodies raised against the particular SSX-2 epitopes was also assessed by BLAST protein search. As described in the Examples, specificity of the $SSX-2_{41-49}$ and $SSX-2_{120-128}$ monoclonal antibodies to the SSX-2 protein was assessed by determining the minimal region of the $SSX-2_{41-49}$ epitope and $SSX-2_{120-128}$ epitope recognized by the respective monoclonal antibodies. Short peptide sequences from overlapping segments of the amino acid sequence of 41-49 (SEQ ID NO:3) or 120-128 (SEQ ID NO:4) of the SSX-2 protein were analyzed for competitive binding with the $SSX-2_{41-49}$ and $SSX-2_{120-128}$ immunogen, respectively. In some embodiments, the minimal region of $SSX-2_{41-49}$ epitope recognized by the $SSX-2_{41-49}$ monoclonal antibody is 45-48. In some embodiments, the minimal region of $SSX-2_{120-128}$ epitope recognized by the $SSX-2_{120-128}$ monoclonal antibody is 123-128. BLAST protein search revealed that no other human proteins share the minimal amino acid sequence of $SSX-2_{41-49}$ epitope or $SSX-2_{120-128}$ epitope.

Additionally, given that there are 8 other members of the SSX family of proteins having similar peptide sequences corresponding to amino acid 41-49 and 120-128 of the SSX-2 protein, the corresponding peptides of these SSX family proteins were analyzed to determine cross reactivity with the SSX-2 epitopes recognized by the SSX-2 monoclonal antibodies disclosed. No cross-reactivity of $SSX-2_{41-49}$ epitope with peptides corresponding to other SSX family proteins was indicated. This clearly demonstrates a very high degree of specificity. However, partial cross-reactivity of $SSX-2_{120-128}$ epitope was noted with peptides corresponding to other SSX family proteins, and this partial cross-reactivity relates to SSX-3.

In some embodiments, specificity of the $SSX-2_{41-49}$ and $SSX-2_{120-128}$ monoclonal antibodies was further analyzed by IHC staining of a variety of tumor tissues in a peptide competition assay, as described herein. In the presence of an excess amount of SSX-2 peptide, (such as at least 2 fold, or at least 4 fold, or at least 6 fold, or at least 8 fold, or at least 10 fold, but not limited to such), the $SSX-2_{41-49}$ and $SSX-2_{120-128}$ monoclonal antibodies exhibit competitive binding. It is noted that although an antibody of the disclosure may cross react (e.g., partially) with other proteins, such proteins may not be expressed or only minimally expressed in a particular tissue or cell and would therefore not influence the competitive binding.

The specificity of the SSX-2 antibodies is relevant in relation not only to immunohistochemical analysis but also to a broad range of other analytical techniques in which these antibodies can be employed in detection of the SSX-2 antigen in a sample. For instance, if the antibody is used in an analysis of protein expression in a particular cell or tissue, such as a cancerous cell or a tumor, the high specificity of the antibody will minimize the number of false positive results, thus leading to a more reliable analysis. In embodiments herein, the SSX-2 monoclonal antibodies of the disclosure, $SSX-2_{41-49}$ or $SSX-2_{120-128}$, have utility as diagnostic tools in that each can complement cancer therapies that target the SSX-2 tumor associated antigen. In some embodiments, the SSX-2 monoclonal antibodies of the disclosure can be utilized in standard assays such as, ELISA, FACS analysis, immunohistochemistry, immunocytology and immunohistology assays, immunoprecipitation and Western blotting to detect the expression of the SSX-2 antigen in tumor tissues or cancerous cells.

In an effort to obtain the expression profile of tumors of interest, a method of detecting the levels of expression of specific tumor associated antigens in tumor tissue was developed. Determination of the relative amounts of a TAA in tumor tissues requires an assay with high specificity and sensitivity. Accordingly, monoclonal antibodies having a high degree of specificity and utility as an antibody in an assay (e.g., the primary antibody in an assay) were developed. in addition to having a high degree of specificty, the monoclonal antibodies disclosed herein give significantly less background staining than polyclonal antibodies when detecting antigens in tissue. As such, using the monoclonal antibodies described herein, a better assessment can be made regarding the types of cells that express the antigen of interest, and the percentage of positive expressing cells is not underestimated over the total tissue.

In some embodiments, monoclonal antibodies disclosed herein are generated with a peptide immunogen. In some instances, peptide immunogens have advantages over whole proteins in that the antibodies generated can be targeted to unique sequence regions. This is particularly useful when investigating proteins that belong to families of high sequence homology. Thus, embodiments of the disclosure utilize peptide immunogens of 8-15 amino acids in length, such as immunogens of 8 amino acids in length, or immunogens of 9 amino acids in length, or immunogens of 10 amino acids in length, or immunogens of 11 amino acids in length, or immunogens of 12 amino acids in length, or immunogens of 13 amino acids in length, or immunogens of 14 amino acids in length, or immunogens of 15 amino acids in length. Such a peptide can be an epitope of a larger antigen. Thus, in some embodiments, the disclosure provides monoclonal antibodies targeted to a particular epitope, wherein the antibody is generated using a peptide immunogen incorporating the sequence of that epitope.

In some embodiments, the disclosure provides a monoclonal antibody directed against PRAME or SSX-2 antigen that binds an epitope having an amino acid sequence of SEQ ID NO:1 or SEQ ID NO:2 and SEQ ID NO:3 or SEQ ID NO:4, respecitively.

Thus, in some embodiments, the disclosure provides a monoclonal antibody directed against PRAME antigen that binds an epitope comprising amino acid sequence of SEQ ID NO:1 or SEQ ID NO:2. In some embodiments, the antibody is specific to the $PRAME_{123-132}$ eptiope. In some embodiments the antibody is specific to the $PRAME_{276-286}$ eptiope.

PRAME (preferentially expressed antigen in melanoma), also known as MAPE, DAGE, and OIP4, was originally observed as a melanoma antigen. Subsequently, it has been recognized as a CT antigen, but unlike many CT antigens (e.g., MAGE, GAGE, and BAGE) it is expressed in acute myeloid leukemias. PRAME is a member of the MAPE family which consists largely of hypothetical proteins with which it shares limited sequence similarity. PRAME is also an important modulator of retinoic acid signaling (Epping et al., Cell 122(6):835-847, 2005). PRAME has been shown to be a useful tool for detecting minimal residual disease (Proto-Siqueira et al., Leukaemia Res. 27(5):393-396, 2003; Matsushita et al., Methods Mol. Med. 97:267-275, 2004; and Matsushita et al., Br. J Haematol. 112(4):916-926, 2001). The usefulness of PRAME as a TuAA is taught in U.S. Pat. No. 5,830,753 entitled "ISOLATED NUCLEIC ACID MOLECULES CODING FOR TUMOR REJECTION ANTIGEN PRECURSOR DAGE AND USES THEREOF", which is hereby incorporated by reference in its entirety. U.S. patent application Ser. No. 10/181,499 (Publication No. U.S. 2003-0186355 A1), entitled "METHODS FOR SELECTING AND PRODUCING T CELL PEPTIDE EPITOPES AND VACCINES INCORPORATING SAID SELECTED EPITOPES" (which is incorporated herein by reference in its entirety) identifies a variety of potential epitopes, including PRAME 276-286 using in vitro digestion with immunoproteasome. U.S Pat. No. 6,861,234 entitled "METHOD OF EPITOPE DISCOVERY"; and U.S. Pat. No. 7,511,119 entitled "PRAME PEPTIDE ANALOGUES" disclosing PRAME epitopes is each incorporated herein by reference in its entirety.

PRAME expression is noted in the nucleus. In addition to being expressed in acute myeloid leukemias, PRAME is also known to be expressed in solid, soft tissue, hematological and metastatic tumors. PRAME is also highly expressed in a number of conditions and/or diseases such as, but not limited to, breast, ovarian, prostate, melanoma, pancreatic, renal, and colorectal cancers. PRAME is also highly expressed in lymphomas including Hodgkin's lymphomas, peripheral T/NK cell lymphomas, anaplastic large cell lymphomas, and peripheral B cell lymphomas, but not in non-Hodgkin's lymphomas. High expression of PRAME has been noted in synovial sarcomas. PRAME is also highly expressed in colon carcinomas and liver metastasis from colorectal cancer and can be a viable target for metastatic colorectal cancer as well as for metastatic disease in other cancers.

In some embodiments, the disclosure provides a monoclonal antibody directed against SSX-2 antigen that binds an epitope comprising or consisting essentially of an amino acid sequence of SEQ ID NO:3 or SEQ ID NO:4. In some embodiments, the antibody is specific to the SSX-2$_{41-49}$ epitope. In some embodiments, the antibody is specific to the SSX-2$_{120-128}$ epitope.

SSX-2, also known as Hom-Mel-40, is a member of a family of highly conserved cancer-testis antigens (Gure, A.O. et al. Int. J. Cancer 72:965-971, 1997, which is hereby incorporated by reference in its entirety). Its identification as a TuAA antigen is taught in U.S. Pat. No. 6,025,191 entitled "ISOLATED NUCLEIC ACID MOLECULES THAT ENCODE A MELANOMA SPECIFIC ANTIGEN AND USES THEREOF," which is hereby incorporated by reference in its entirety. It is noted that cancer-testis antigens are found in a variety of tumors, but are generally absent from normal adult tissues except testis. Six (SSX-1, 2, 3, 4, 5, and 7) of the nine members of the SSX family have been shown to be transcribed in testis; of these, only SSX-1, 2, and 4 show significant expression in cancer. SSX-5 is only rarely expressed (approximately in 1% of the tumors examined), and SSX-3 expression has only been shown in sarcomas. SSX cancer testis antigens are expressed in most multiple myeloma patients. Of the SSX molecules involved in cancer, SSX-2 showed the strongest correlation with reduced survival (Taylor et al., J. Immunotherapy 2005, which hereby is incorporated by reference in its entirety).

SSX-2 is expressed in many different types of tumors, including synovial sarcomas, melanoma, head and neck, breast, stomach, lung, pancreatic, gallbladder, uterine/cervix, malignant lymphoma and melanoma, renal, thyroid, colon and ovarian cancers, but is not limited to such. In addition to its widespread expression in a variety of cancers, it is also immunogenic in patients with late stage disease. Further, there is evidence of spontaneous humoral and cellular immune responses towards this antigen in metastatic tumor patients (Ayyoub M, et al., Cancer Res. 63(17): 5601-6, 2003; Ayyoub M, et al., J Immunol. 168(4): 1717-22, 2002), each of which is incorporated herein by reference in its entirety. Two HLA-A2 restricted T cell epitopes have been identified recently using reverse T-cell immunology, namely SSX-2$_{41-49}$ (Ayyoub M, et al. J Immunol. 168(4): 1717-22, 2002; U.S. Pat. No. 6,548,064, entitled "ISOLATED PEPTIDES CONSISTING OF AMINO ACID SEQUENCES FOUND IN SSX OR NY-ESO-1 MOLECULES, THAT BIND TO HLA MOLECULE"; U.S. patent application Ser. No. 10/117,937 (Publication No. U.S. 2003-0220239 A1), entitled "EPITOPE SEQUENCES") and SSX-2$_{103-111}$ (Wagner C, et al. Cancer Immunity 3:18, 2003), each of which is incorporated herein by reference in its entirety. U.S. patent application Ser. No.: 11/156,253, (Publication No. 2006-0063913), entitled "SSX-2 PEPTIDE ANALOGS" which discloses SSX-2 epitopes is incorporated by reference in its entirety.

Antibodies can be generated or produced using a number of techniques such as, for example, cell culture techniques, or via transfection of antibody genes into suitable bacterial, fungal (e.g., yeast), insect, or mammalian cell hosts in order to allow for the production of recombinant antibodies. Monoclonal antibodies can be raised by fusion of B lymphocytes with immortal cell cultures to produce hybridomas that can produce many copies of the exact same antibody.

Exemplary monoclonal antibodies disclosed herein are raised against peptide antigens that recognize a more specific epitope than those raised against the full protein. In some embodiments, monoclonal antibodies specific for PRAME$_{123-132}$, PRAME$_{276-286}$, SSX-2$_{41-49}$, or SSX-2$_{120-128}$ epitopes can be prepared, for example, using the technique of Kohler and Milstein, (Eur. J. Immunol. 6:511-519, 1976, which is hereby incorporated by reference in its entirety), with improvements thereto as appropriate. Briefly, these methods involve the preparation of immortal cell lines capable of producing antibodies having the desired specificity (i.e. reactivity with the peptide antigen of interest as compared to one or more control molecules, for example, unspecific proteins or peptides with overlapping sequence homology). Such cell lines can be produced, for example, from spleen cells obtained from an animal, (e.g., mice, rats, rabbits, sheep or goats, but not limited to such) immunized according to a predetermined schedule incorporating one or more booster immunizations, as described in the Examples. The spleen cells are then immortalized by, for example, fusion with a myeloma cell fusion partner (for example, NSO cells, Sp2 cells and the like), in some instances one that is syngeneic with the immunized animal. A variety of fusion techniques well known in the art can be employed. For example, the spleen cells and myeloma cells can be combined with a nonionic detergent for a few minutes and then plated at low density on a selective medium that supports the growth of hybrid cells, but not myeloma cells. In some embodiments, a selection technique such as HAT (hypoxanthine, aminopterin, thymidine) medium selection, a methodology well known in the art, can be used. After a sufficient time, usually about 1 to 2 weeks, colonies of hybrids are observed. Single colonies are selected and their culture supernatants tested for binding activity against PRAME or SSX-2 peptide antigen. Hybridomas having high reactivity and specificity are preferred. In some embodiments, the disclosure provides a hybridoma for producing a monoclonal antibody that binds to a peptide having the sequence of SEQ ID NO:1 or SEQ ID NO:2 or SEQ ID NO:3 or SEQ ID NO:4. Greater details on producing hybridomas in line with the disclosure are discussed in the Examples herein.

Once hybridomas are generated, monoclonal antibodies can be isolated from the supernatants of growing hybridoma colonies; though in some embodiments, the supernatants can be used directly. In addition, various techniques can be employed to enhance the yield, such as injection of the hybridoma cell line into the peritoneal cavity of a suitable vertebrate host, such as a mouse. Monoclonal antibodies can then be harvested from the ascites fluid or blood. Contaminants can be removed from the antibodies by conventional techniques, such as, for example, chromatography, gel filtration, precipitation, and extraction as are well known to the skilled artisan.

In some embodiments, the disclosure provides a method of detecting expression of PRAME and/or SSX-2 antigen in a sample comprising contacting a biological sample from a subject with an antibody specific to one or more of the $PRAME_{123-132}$ epitope, or the $PRAME_{276-286}$ epitope, or the $SSX-2_{41-49}$ epitope, or the $SSX-2_{120-128}$ epitope; and detecting antibody bound to the sample thereby detecting expression of the PRAME or SSX-2 antigen. In some embodiments, the disclosure relates to a method of detecting cancerous cells or tissues or portions thereof in a biological sample, for example, histological or cytological specimens, biopsies, and the like. This method involves providing an antibody, such as a PRAME or SSX-2 antibody disclosed herein, that can be attached to a label (i.e. a detectable marker) that permits the detection of the cells or tissues (for example, PRAME or SSX-2 or fragments thereof associated with or expressed by such cancerous cells) upon binding of the PRAME or SSX-2 antibody to the antigen in the cells or tissues. The biological sample can be contacted with the labeled PRAME or SSX-2 antibody under conditions effective to permit binding of the PRAME or SSX-2 antibody to the PRAME or SSX-2 protein of any of the cells or tissues in a sample.

In some embodiments, a PRAME or SSX-2 antibody as disclosed herein can be linked to a detectable marker. Useful detectable markers with which a PRAME or SSX-2 antibody of the disclosure can be labeled to include fluorescent compounds, various enzymes, prosthetic groups, luminescent materials, bioluminescent materials, fluorescent emitting materials and the like. Examples of fluorescent detectable markers include fluorescein, fluorescein isothiocyanate, rhodamine, dichlorotriazinylamine fluorescein, 5-dimethylamine-1-napthalenesulfonyl chloride, phycoerythrin, quantum dots, and the like. An antibody can also be labeled with detectable enzymes, such as alkaline phosphatase, horseradish peroxidase, beta-galactosidase, acetylcholinesterase, glucose oxidase, and the like. When an antibody is labeled with a detectable enzyme, it is detected by adding additional reagents that the enzyme acts upon to produce a detectable reaction product (for example, colored, fluorescent, or luminescent). For example, when the detectable agent horseradish peroxidase is present, the addition of hydrogen peroxide and/or diaminobenzidine leads to a colored reaction product, which is detectable. An antibody can also be labeled with a prosthetic group (e.g., one of the streptavidin/biotin pair, one of the avidin/biotin pair, and the like). For example, an antibody can be labeled with biotin, and detected through measurement of avidin or streptavidin binding, wherein the avidin or streptavidin is conjugated to a detectable marker (e.g., fluorescent compounds, various enzymes, prosthetic groups, luminescent materials, bioluminescent materials, fluorescent emitting materials and the like). Luminescent materials can include luminol; and examples of bioluminescent materials include luciferin, and aequorin. Methods of linking a detectable marker to an antibody are known to those of skill in the art and can be for example, by chemical coupling, gene fusion, noncovalent association, or the like.

In some embodiments, the PRAME and SSX-2 antibodies can be used diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

Diagnostic or experimental techniques for which the PRAME and SSX-2 antibodies disclosed herein can be applicable include, in a non-limiting manner, immunohistochemial assays, ELISA assays, flow cytometry, Western Blotting assays, and the like. It is typical that such assays involve use of secondary reagents carrying the label or label generating moiety. The use of a secondary reagent can be advantageous in that it can offer signal amplification compared to direct labeling, and it can require production of only a single detectable reagent usable with a wide variety of primary reagents. In some embodiments, the primary reagent (antibody) can be directly labeled. Such embodiments reduce the number of steps required to carry out the assay and can also result in lower backgrounds.

For example, immunohistochemical staining allows the visualization of antigens via the sequential application of a specific antibody (primary antibody) that binds to the antigen; a secondary antibody, or other secondary reagent, that binds to the primary antibody, with an enzyme complex linked or conjugated to the secondary reagent; and a chromogenic substrate; with washing steps in between. The enzymatic activation of the chromogen results in a visible reaction product at the antigen site. The specimen can then be counterstained and cover slipped. Results can be interpreted using a light microscope and aid in the differential diagnosis of pathophysiological processes, which may or may not be associated with a particular antigen. In some embodiments, the clinical interpretation of any staining, or the absence of staining, can be complemented by morphological studies and evaluation of proper controls. In some embodiments, evaluation can be made by a skilled artisan (e.g., a qualified pathologist). In some embodiments, the secondary reagent can be linked to a flouorescent molecule.

In some embodiments, the PRAME or SSX-2 antibodies disclosed herein can be used in immunofluorescence techniques to examine human tissue, cell, and bodily fluid specimens. For example, slides containing cryostat sections of frozen, unfixed tissue biopsy samples or cytological smears can be air dried, formalin or acetone fixed, and incubated with a PRAME or SSX-2 monoclonal antibody disclosed herein, in a humidified chamber at room temperature. The slides can then be washed and further incubated with a preparation of a secondary antibody directed against the PRAME or SSX-2 monoclonal antibody. In some embodiments, the monoclonal antibodies used are derived from the fusion of a mouse spleen lymphocyte and a mouse myeloma cell line, and the secondary antibody can be an anti-mouse immunoglobulin. This secondary antibody is tagged with a compound (e.g., labeled with a detectable marker), for instance rhodamine or fluorescein isothiocyanate, that fluoresces at a particular wavelength. The staining pattern and intensities within the sample are then determined by fluorescent light microscopy and optionally photographically recorded.

In some embodiments, flow cytometry can be used to examine tissue specimens or exfoliated cells, i.e. single cell preparations from aspiration biopsies of tumors, using the PRAME or SSX-2 antibodies disclosed herein. In some embodiments, the PRAME or SSX-2 antibodies disclosed herein can be useful in quantitation of live tumor cells, i.e. single cell preparations from aspiration biopsies of tumors, by computer enhanced fluorescence image analyzer or with a flow cytometer. In some embodiments, the antibodies disclosed herein can be useful in such assays to differentiate benign from malignant tumors as the PRAME or SSX-2 protein to which the PRAME or SSX-2 antibodies bind is expressed in increased amounts by malignant tumors as compared to benign tumors. The percent PRAME or SSX-2 positive cell population, alone or in conjunction with determination of other attributes of the cells (e.g., DNA ploidy of these cells), can, additionally, provide very useful information for determining a treatment or regimen. Methods of flow cytometry are well known in the art.

PRAME or SSX-2 antibodies disclosed can be further tested for reactivity with PRAME or SSX-2 antigen respectively by Western blotting. For example, cell extracts can be prepared and subjected to sodium dodecyl sulfate (SDS) polyacrylamide gel electrophoresis. After electrophoresis, the separated antigens can be transferred to nitrocellulose membranes, blocked with mouse serum (e.g., 20%), and probed with the PRAME or SSX-2 monoclonal antibodies described herein. In some embodiments, antibody binding can be detected using, for example, anti-mouse or anti-goat specific secondary antibody linked to alkaline phosphatase and developed with the appropriate substrate. Western protocols are well known in the art.

In some embodiments, a capture assay can be used to detect and quantitate the antibodies disclosed or antigens recognized thereby, and to assess the epitopes recognized by the antibodies. This methodology is well known in the art and can be modified to assess antibody competition in a competition immunoassay. Generally, these methodologies can employ an unlabeled antigen immobilized on a solid phase, (for example, a microtiter plate) to which and antibody is allowed to bind. The antibody can be directly labeled. The antibody can be detected by a secondary reagent that is labeled that specifically recognizes the antibody. The strength of the signal detected (for example, by measuring absorbance) is indicative of the amount of the antibody bound. Thus, the presence of PRAME or SSX-2 can be assayed in a sample by a competition immunoassay. This assay provides an alternative to labeling the PRAME or SSX-2 antibodies disclosed herein, utilizing standards (for example, appropriate secondary antibodies) labeled with a detectable substance and an unlabeled PRAME or SSX-2 antibody. In this assay, the biological sample, the labeled standards and the PRAME or SSX-2 binding agent are combined and the amount of labeled standard bound to the unlabeled antibody is determined. The amount of PRAME or SSX-2 in the sample is inversely proportional to the amount of labeled standard bound to the PRAME or SSX-2 binding agent.

In some embodiments the disclosure provides kits comprising the PRAME and/or SSX-2 antibodies disclosed herein and instructions for use. The kits can further contain at least one additional reagent, such as one or more additional antibodies disclosed or one or more reagents appropriate to a particular diagnostic protocol or assay.

In some embodiments, kits containing the antibodies or antigen-binding fragments thereof of the disclosure can be prepared for in vitro diagnosis of cancer by immunohistology, immunocytology and other such methods described above. The components of the kits can be packaged either in aqueous medium or in lyophilized dry powder form. When the PRAME and/or SSX-2 antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates, or as separate moieties to be conjugated by the user or the kit.

Some embodiments relate to a kit comprising a carrier being compartmentalized to receive in close confinement therein one or more container means or series of container means such as test tubes, vials, flasks, bottles, syringes, or the like. In some embodiments, a first of said container means or series of container means can contain one or more PRAME and/or SSX-2 antibodies or antigen-binding fragments thereof or other reagent. In some embodiments, a second container means or series of container means can contain a label or linker-label intermediate.

The following embodiments and aspects thereof are described and illustrated in conjunction with compositions and methods which are meant to be exemplary and illustrative, not limiting in scope.

EXAMPLES

The following examples are included to demonstrate embodiments disclosed herein. It is appreciated by those of skill in the art that the methodology and compositions disclosed in the examples which follow represent methodology discovered by the inventors to function well in the practice of the disclosure, and thus can be considered to constitute particular modes for its practice. However, those of skill in the art can, in light of the disclosure, appreciate that many changes can be made in the specific embodiments which are disclosed and still obtain a like or similar result without departing from the spirit and scope of the disclosure.

Example 1

Materials and Methods

Peptides. $PRAME_{123-132}$ (SEQ ID NO:1), $PRAME_{276-286}$ (SEQ ID NO:2), $SSX-2_{41-49}$ (SEQ ID NO:3) and $SSX-2_{120-128}$ (SEQ ID NO:4). For coupling of the cysteine containing peptide $PRAME_{276-286}$ (Cys 286, ISPEKEEQYIC (SEQ ID NO:5)) to maleimide activated KLH (Keyhole Limpet Hemocyanin) for immunization, the last amino acid was changed from cysteine to alanine to make conjugation easier.

Conjugation of peptides to KLH for immunization in mice. Reconstituted 2.0 micrograms maleimide-activated KLH (ma-KLH, Pierce—Rockford, Ill., USA) in 0.25 milliliters water to 8 micrograms per milliliter. Added 0.25 ml of 8 micrograms per milliliter of ma-KLH to 1 micromole of $PRAME_{123-132}$, $PRAME_{276-286}$, $SSX-2_{41-49}$ or $SSX-2_{120-128}$ peptide, mixed, added up to 0.25 milliliters $H_2O$ if the peptide was not completely dissolved in 1 minute. Incubated for 2 hours at room temperature then added 1.5 milliliters of 0.1 M Na-Phosphate buffer, pH 8.0, and mixed. Incubated for 2 hours at room temperature and added 12 ml of PBS (phosphate-buffered saline; Invitrogen™—Carlsbad, Calif., USA). Concentrated in Millipore Amicon® Ultra 15 centrifugal filter (20 minutes, 4000 grams in horizontal rotor) to 0.5 milliliters and discarded the filtrate. Added 12 milliliters PBS to upper compartment of the filter containing the concentrate. Concentrated again to less than 0.5 milliliters. Reconstituted the concentrate (peptide-KLH conjugate) with PBS to 4 milliliters. Determined the concentration of peptide-KLH conjugate by BCA™ protein assay, well known in the art. Injected conjugate and adjuvant suspension into mice at 2 week intervals until measurable titers were achieved. The material injected was a 1:1 mixture of the peptide-KLH conjugated with Ribi or Freund's Incomplete adjuvant (IFA). The option for using either of the two adjuvant systems was because, in almost all circumstances, information about the antibody response to a specific antigen plus a particular adjuvant system can vary between different types of adjuvants. In the primary immunization, Freund's Complete adjuvant (CFA) can be used. When Freund's Complete adjuvant is used, it can be used for the primary immunization and Freund's Incomplete adjuvant can be used for all subsequent immunizations. The total volume per animal was not more than 0.2 milliliters for subcutaneous administration and not more than 0.5 milliliters for intraperitoneal administration. The total amount of immunogen per animal per immunization can be in the range of 1 to 200 micrograms such as between 10 to 50 micrograms, or between 20 to 60 micrograms, or between 30 to 70 micrograms, or between 40 to 80 micrograms, or between 50 to 90 micrograms, or between 60 to 100 micrograms, or between 70 to 110 micrograms, or between 80 to 120 micrograms, or between 90 to 130 micrograms, or between 100 to 140 micrograms, or between 110 to 150 micrograms, or between 120 to 160 micrograms, or between 130 to 170 micrograms, or between 140 to 180 micrograms, or between 150 to 190 micrograms, or between 160 to 200 micrograms, depending on the protein's immunogenicity.

Immunohistochemical staining of paraffin tissue sections with a primary antibody disclosed herein. Staining Procedure for the monoclonal antibodies disclosed herein encompasses: 1). Deparaffinization using EZ-AR™ common solution (Biogenex—San Ramon, Calif., USA) at 70° C. for 10 minutes in preheated solution followed by 20 minutes cooling down at room temperature (RT). 2). Antigen Unmasking was then achieved with Citra Plus antigen retrieval solution (Biogenex) at pH 5.5, for 2 minutes; the sample was then placed in the Decloaking Chamber™ (BioCare—Concord, Calif., USA), at 120-125° C. for 10-15 minutes at 18 psi; followed by incubation in Sniper (Nemesis™; BioCare) solution for 10 minutes at room temperature (½ dilute). 3). Primary antibody was then bound for 45 minutes in DAKO™ background reducing diluent. 4). Followed by secondary antibody (Nemesis™ Probe) binding for 15 minutes followed by Nemesis™ Polymer (amplification of binding) for 30 minutes 5). DAKO™ detection substrate DAB (3',3'-diaminobenzidine) was then applied for 10 minutes. 6). Slides were then counterstained with hematoxylin, (5-10 dips). 7), followed by post counterstain with Bluing reagent, for 1 minute then washed with water followed by a dehydration step with 100% alcohol 3× for 1 minute each then a final step with xylene 3× for 1 minute. 8). Slides were then cover slipped using the Sakura automated machine.

Monoclonal Antibodies. The monoclonal antibodies disclosed herein have been optimized for use in immunohistochemical staining with Nemesis™ detection kits and automated slide stainers, but is not limited to such. Each step in the staining protocol included incubation for a precise period of time. At the end of each incubation step, the sections were rinsed by the Nemesis™ automated slide stainer to stop the reaction and remove unbound material that would hinder the desired reaction in subsequent steps. To minimize evaporation of the aqueous reagents from the specimen containing slide, a coverslip solution was applied in the slide stainer. Staining was completed after incubation with a substrate chromogen and optional counterstaining. A working concentration of the monoclonal antibodies disclosed, in immunohistochemistry procedures, was 200 nanograms per milliliter of mouse monoclonal antibody directed against SSX-2 and 10 micrograms per milliliter of mouse monoclonal antibody directed against PRAME. The antibodies were diluted in TBS (Tris-Buffered Saline) buffer (Invitrogen) containing 0.02% sodium azide as a preservative.

ELISA Assay. In order to detect an antibody directed against PRAME or SSX-2 peptide antigen disclosed herein, the ELISA method was utilized. The peptide antigen was placed at a concentration of 0.5 micrograms per well of the protein in a 96-well NUNC MaxiSorp® plate (eBioscience, Inc., San Diego, Calif., USA). The plate was left at room temperature for 1 hour, so as to cause binding of the peptide to the plate, followed by incubation at 4° C. overnight. The plate was washed with a wash buffer (PBS supplemented with 0.050% TWEEN 20, 5 millimolar imidazole, and 500 millimolar NaCl) and blocked with a blocking buffer (wash buffer supplemented with casein and goat serum). The sample containing $PRAME_{123\text{-}132}$ or $PRAME_{276\text{-}286}$, or $SSX\text{-}2_{41\text{-}49}$ or $SSX\text{-}2_{120\text{-}128}$ antibody was added to the wells and allowed to react for 30 minutes, and the plate was washed. A secondary antibody (peroxidase-labeled goat anti-rat IgG antibody, Sigma—St. Louis, Mo., USA) was added and incubated for 30 minutes, the plate was next washed. An enzyme reaction was carried out by addition of a chromogenic substrate (TMB Microwell Peroxidase Substrate System, (KPL—Gaithersburg, Md., USA)) and then terminated with 1 molar phosphoric acid. Absorbance was measured at 635 nm.

Plates for screening clones by ELISA. Maxisorp plates (NUNC Maxisorp® stripwells (8)), were coated with $PRAME_{123\text{-}132}$ (SEQ ID NO:1), or $PRAME_{276\text{-}286}$ (SEQ ID NO:2), or $SSX\text{-}2_{43\text{-}49}$ (SEQ ID NO:3) or $SSX\text{-}2_{120\text{-}128}$ (SEQ ID NO:4) peptide-ovalbumin conjugate for screening of clones by ELISA. The peptide-ovalbumin conjugate (100 microliters of 10 micrograms per milliliters solution) for each was placed into each well designated for the antigen and the cys-ovalbumin conjugate (100 microliters of 10 micrograms per milliliters solution in 20 millimolar Na2B4O7 pH 9.5) was placed into each well designated to be the blank or control well. The plate was incubated at room temperature for 16-20 hours; washed twice with $H_2O$ and blocked with 0.2 milliliter per well of ELISA diluent (2% goat serum, 5 micrograms per milliliter casein, 0.1% $NaN_3$ in TBS pH 8.0) for 3 hours. The plates were washed twice with $H_2O$, dried and stored either at room temperature for 4 to 16 hours (then covered with foil) or at 4° C. or lower.

Detection of an antibody that binds to specific PRAME or SSX-2 epitopes. In order to detect an antibody directed against PRAME or SSX-2 epitope by ELISA, each peptide antigen was dissolved in a carbonate buffer (0.15% $Na_2CO_3$ and 0.3% $NaHCO_3$) and placed at a concentration of 1 or 2 micrograms per well of the peptide in a 96-well plate (Nunc MaxiSorp®). The plate was left overnight at 4° C. so as to cause adsorption of the peptide onto the plate. The plate was washed with PBS and blocked with PBS supplemented with 0.5% bovine serum albumin. The sample containing the antibody to specific PRAME or SSX-2 epitopes; $PRAME_{123\text{-}132}$ (SEQ ID NO:1), or $PRAME_{276\text{-}286}$ (SEQ ID NO:2), or $SSX\text{-}2_{41\text{-}49}$ (SEQ ID NO:3) or $SSX\text{-}2_{120\text{-}128}$ (SEQ ID NO:4), respectively, was added to the wells after dilution and allowed to react with the peptide for 1 hour. The plate was then washed with PBS containing 0.05% TWEEN 20. A secondary antibody was added to the wells and allowed to react therewith for 30 minutes; the plate thereafter was washed with PBS containing 0.05% TWEEN 20. A chromogenic reaction and measurement of absorbance were carried out as above.

Scoring of staining intensity in tissue samples by Immunohistochemistry. The histology of all tissue samples was assessed by a pathologist. The expression (based on intensity of staining) of PRAME or SSX-2 as noted in all samples tested was scored according to the pathologist's assessment and assigned a grade of 0 to 3+, indicative of the level of intensity. A '0' grade indicates no intensity of staining, or expression of the antigen recognized by the antibody, was observed. A grade of '1+' indicates a weak intensity of staining or expression of the antigen recognized by the antibody. A grade of '2+' indicates a moderate intensity of staining or expression of the antigen recognized by the antibody. A grade of '3+' indicates a strong intensity of staining or expression of the antigen recognized by the antibody.

Quantitative Real Time Polymerase Chain Reaction (QRT-PCR) Quantitative RT-PCR, well known to one of skill in the art, was used to determine the expression frequency of PRAME and SSX-2 in various tumor and normal tissues. In brevity, messenger RNA isolated from tumor and normal tissues were reverse transcribed and the cDNA amplified using real-time PCR reactions. Briefly, a quantitative RT-PCR assay was developed utilizing Taqman technology, which takes advantage of Taq polymerase's ability to cleave a probe with its exonuclease activity during a PCR reaction (see, for example, Bustin, S. A., J. Mol. Endocrin. 25:169-193; 2000). The probe was approximately 20-30 bases in length and was attached to a fluorescent dye at the 5' end and a quencher dye at the 3' end. As polymerization proceeds, the properly annealed probe can be degraded by the polymerase, thus separating the fluorophore from the quencher. Increased fluorescence was directly proportional to an increase in amplification of the PCR product, thus enabling quantitation. Data analyses of real-time PCR was based on relative quantitation of gene expression using the ΔCt or comparative Ct method, in which expression is relative to the housekeeping gene GAPDH, assuming that the efficiencies for both genes are similar.

Example 2

Generation of Monoclonal Antibodies (mAbs) to PRAME and SSX-2 Epitopes

A typical hybridoma methodology encompassing immunization, fusion, cloning and hybridoma stabilization phases was utilized in generating monoclonal antibodies directed against PRAME and SSX-2 antigens for diagnostic purposes. These monoclonal antibodies are specific to $PRAME_{123-132}$, $PRAME_{276-286}$, $SSX-2_{41-49}$, and $SSX-2_{120-128}$ epitopes. Briefly, the monoclonal antibodies were generated as follows: female Swiss Webster (CFW®) mice were immunized intraperitoneally (ip) with PRAME or SSX-2 immunogen emulsified with Freund's complete adjuvant (CFA). Subsequent injections followed a two-week interval with IFA, incomplete Freund's adjuvant, in which samples were drawn ten days after each injection. The animals' responses to immunogen were assessed by ELISA.

Mouse Immunization Phase Protocol. On day 0, female CFW Mice were pre-bled (~0.1 ml serum/mouse), and intraperitoneally (ip) injected with 100 micrograms of the immunogen comprising PRAME or SSX-2 with Freund's complete adjuvant (CFA). At two-week intervals thereafter, mice received a boost IP of 50 micrograms immunogen with IFA. Mice were subsequently bled ten days following each immunization (~0.1 milliliter blood/mouse) and the serum analyzed by ELISA for response to the immunogen for several cycles, until high serum titers were achieved.

Following immunization, activated spleen cells from hyper-immunized mice (mice boosted with an additional 10 micrograms of immunogen administered interperitoneally (ip) and 5 micrograms of immunogen administered intravenously (iv)) were prepared and fused to NSO myeloma cells using polyethylene glycol. The fused cells were then resuspended in pre-warmed complete NSO/pyruvate medium (NSO (Gibco®-Invitrogen™) supplemented with 1% non-essential amino acid, 2 millimolar L-glutamine, 100 units per milliliter penicillin and 100 micrograms per milliliter streptomycin), plated and cultured under conditions of 5% CO2, relative humidity of 100%, and 37° C. The cells were monitored and treated with NSO/pyruvate/2x Hypoxanthine Aminopterin and Thymidine (HAT) medium on day 1 followed by NSO/pyruvate/1xHAT medium on subsequent days. Two weeks later, cells were treated with NSO/pyruvate/1xHypoxanthine and Thymidine (HT) and viable hybridomas were selected, supernatants collected and screened for antigen specific antibodies by ELISA. The antibody secreting hybridomas with the highest specificity in the initial ELISA screen were grown and temporarily frozen. Media from positive hybridomas was evaluated.

A few hundred positive selected primary clones were expanded and sub-cloned. Wells with growing cells were screened for antibody secretion by ELISA. Hybridoma culture supernatant containing antibody was evaluated through functional assay such as immunohistochemistry (IHC) assay discussed elsewhere herein. A few dozen positive sub-clones with the highest specificity were frozen in duplicate vials.

A clone was selected to be sub-cloned to generate a stable, third generation cell line. The growing cells were screened for antigen specific antibody by ELISA. The media samples from up to ten positive clones were evaluated and the clones were frozen. One cell line was selected for final expansion for long term storage or scale up by in vitro methods. Based on storage conditions tested, the antibody supernatants were found to be best when stored at 2-8° C. without freezing, once scaled up and antibody was purified from the supernatants, the antibodies were aliquoted and stored at −20° C.

Using the methodology described supra, clones to PRAME276-286 (clone 3-2-1-21), PRAME123-132 (clone 3-15-14-2), $SSX-2_{41}$-49 (1-42-9), and $SSX-2_{120}$-128 (clone 4-7-12) were obtained and analyzed.

Hybridomas secreting antibody to $PRAME_{123-132}$, $PRAME_{276-286}$, $SSX-2_{41-49}$, and $SSX-2_{120-128}$ have been deposited pursuant to, and in satisfaction of, the requirements of the Budapest Treaty on the International Recognition of the Deposit of Microorganisms for the Purposes of Patent Procedure with the American Type Culture Collection ("A.T.C.C.") at 10801 University Boulevard, Manassas, Va. 20110-2209. Mouse anti-human $PRAME_{123-132}$ monoclonal antibody hybridoma clone (3-15-14-2) was deposited, and received A.T.C.C. Designation Number PTA 11099. Mouse anti-human $PRAME_{276-286}$ monoclonal antibody hybridoma clone (3-2-1-21) was deposited, and received A.T.C.C. Designation Number PTA11101. Mouse anti-human $SSX-2_{41-49}$ monoclonal antibody hybridoma clone (1-42-9-1) and mouse anti-human $SSX-2_{120-128}$ monoclonal antibody hybridoma clone (4-7-12) were each deposited, and received A.T.C.C. Designation Numbers PTA11102 and PTA11100, respectively. The deposits made are merely as a convenience for those of skill in the art.

Example 3

Minimal Epitope Mapping of PRAME

To determine specificity and whether the antibodies generated recognize distinct or overlapping epitopes on PRAME, minimal epitope mapping was conducted utilizing a simple ELISA capture assay with peptide competition.

Briefly, ELISA plates were pre-coated with the peptide antigen of interest in each well of the microtiter plate and left overnight at 4° C. One row of the plate was left uncoated as a control for nonspecific binding in later steps. The plates were washed twice with TBS (Invitrogen™). Hybridoma supernatant containing the antibody was added to the antigen pre-coated plates and competitive binding of the $PRAME_{276-286}$ antibody to the PRAME antigen was assessed. The PRAME epitope was transferred to the ELISA plate and incubated, alongside the supernatant, for 1 hour at room temperature then discarded, and the plate rinsed five times with TBS. Horseradish peroxidase conjugated goat antibody to mouse IgG was added for 1 hour at room temperature. The plates were washed again and 3,3',5,5'-tetramethylbenzidine dihydrochloride (TMB) substrate (Pierce, Rockford, Ill., USA) added for colorimetric readout at 635 nm using an ELISA plate reader (Molecular Devices, Sunnyvale, Calif., USA).

The results are shown in FIG. 1. FIG. 1 shows serial dilutions of the antibody to various PRAME peptides within the region of amino acids 276 to 286 of the PRAME protein, which were analyzed for competitive binding with the $PRAME_{276-286}$ immunogen. Peptides corresponding to $PRAME_{278-285}$, $PRAME_{279-285}$, $PRAME_{280-285}$, $PRAME_{281-285}$, $PRAME_{276-284}$, $PRAME_{277-285}$, each serially diluted 1:50 (first column), 1:100 (second column), 1:500 (third column) and 1:1000 (fourth column), were analyzed to determine the minimal region of $PRAME_{276-286}$ epitope recognized by the PRAME monoclonal antibody, and the minimal amino acid sequence compared to other known proteins. The data shows that $PRAME_{280-285}$ is the minimal epitope recognized by the $PRAME_{276-286}$ monoclonal antibody. BLAST protein search, showed no other known human protein shares this amino acid sequence. This also indicates the fine specificity of the exemplary $PRAME_{276-286}$ monoclonal antibody to $PRAME_{280-285}$ peptide. However, one of ordinary skill in the art would understand that the minimal epitope that can be recognized by an antibody may not be optimal in terms of other binding characteristics (e.g., binding affinity, and the like). The data therefore suggests that the $PRAME_{276-286}$ antibody is specific to only PRAME protein and is not cross-reactive to any other known human protein. $PRAME_{123-132}$ was also analyzed by BLAST protein search, and no other known human protein shares this amino acid sequence.

Example 4

Determining Antibody Isotype of PRAME Antibodies

Using a similar protocol as the ELISA capture assay described above, ELISA plates were coated with antibodies recognizing various isotypes, such as, IgG1, IgG2, IgG3, IgG4, IgM, and subtypes thereof. An aliquot (1 microgram per milliliter) of the antibody to the $PRAME_{276-286}$ epitope or the antibody to the $PRAME_{123-132}$ epitope (1 microgram per milliliter) in addition to PBS+1% BSA was placed in each well and incubated for 1 hour at room temperature. Then supernatant was discarded and the plate rinsed three times with TBS. HRP-labeled rat anti-mouse Ig mAb was used as a secondary antibody. A colorimetric assay was conducted as described above to determine the isotype of the $PRAME_{276-286}$ and $PRAME_{123-132}$ antibodies. Based on the data obtained, $PRAME_{276-286}$ was found to be an IgG3 antibody and $PRAME_{123-132}$ was found to be an IgG1 antibody.

Example 5

Detection of PRAME Expression in Tissues and Tumor Cells

The PRAME monoclonal antibodies specific to $PRAME_{123-132}$ and $PRAME_{276-286}$ epitopes as described above, were used to analyze tissue samples and tumor cells of various types of cancers by immunohistochemistry (as described in Example 1 above), and determine the expression frequency, by staining intensity.

By immunohistochemical staining with an antibody specific for $PRAME_{276-286}$ epitope, the expression of PRAME tumor-associated antigen in primary tumor tissues of breast, colon, ovary, skin (such as melanoma), pancreas, prostate, liver, renal, lymph node, stomach, brain (such as globalstoma), synovial sarcomas, lung such as (non-small cell lung cancer (NSCLC)), lymphomas, soft tissue sarcomas and metastasic tissues was assessed. Expression of PRAME was also compared to normal adult tissues for each of the tumor tissues analyzed. Tissues from normal testis, (being positive for cancer-testis antigens such as PRAME), was used as a positive control.

As exemplified in Table 1, PRAME was expressed in over 50% of the samples in all of the tumors indicated, by QRT-PCR analysis of both mRNA expression and IHC staining in parallel, except for renal and ovarian cancer in which respectiviely, 40% and 45% of the samples showed positive expression by IHC. Of the ovarian cancers analyzed, PRAME was found to be highly, expressed in ovary clear cell carcinomas and mucinous cyst adenocarcinomas but not in transitional cell carcinomas as per the pathologist's assessment.

The percentage of various cell types of tumor tissue specimens expressing PRAME, as determined by IHC, is shown in Table 2 below. Cell types indicated in Table 2 are represented as follows: Norm—normal cells within the tumor specimen and other cell types infiltrating the tumor; EC—endothelial cells; SM—smooth muscle; Fibro—fibroblast; Stroma; LC—lymphocyte cells; and Nerve cells. The data show no staining of cell type representative of the nerve, stroma or smooth muscle by PRAME antibodies of the disclosure, in any of the cancers tested.

TABLE 1

| Cancers | PRAME Expression QRT-PCR | PRAME Expression IHC |
|---|---|---|
| Ovarian | 94.7% (38 samples) | 45% (33 samples) |
| Breast | 50.0% (30 samples) | 56% (25 samples) |
| Prostate | 71.0% (31 samples) | 70% (27 samples) |
| Colon | 78.9% (38 samples) | 50% (40 samples) |
| Renal | 88.9% (18 samples) | 40% (25 samples) |
| Pancreas | 73.3% (15 samples) | 57% (23 samples) |
| Melanoma | 91.7% (12 samples) | 89% (36 samples) |

TABLE 2

| Cancer | PRAME % Staining of other cell types | | | | | | |
|---|---|---|---|---|---|---|---|
| | Norm | EC | SM | Fibro | Stroma | LC | Nerve |
| Pancreas | 20 | 40 | 0 | 40 | 0 | 50 | 0 |
| Renal | 0 | 12 | 0 | 12 | 0 | 27 | 0 |
| Melanoma | 83 | 50 | 0 | 30 | 0 | 83 | 0 |
| Ovarian | 3 | 43 | 0 | 50 | 0 | 53 | 0 |
| Breast | 30 | 33 | 0 | 20 | 0 | 33 | 0 |
| Prostate | 10 | 48 | 0 | 46 | 0 | 30 | 0 |
| Colorectal | 6 | 23 | 0 | 27 | 0 | 65 | 0 |

Immunohistochemical staining of non-small cell lung cancer tissue specimens (NSCLC) with the antibody specific for the $PRAME_{276-286}$ epitope showed cells from 17/24 NSCLC tumors were positive for PRAME expression. Although the expression was very low, positive expression of 12 of these were only in the inflammatory cells and the chrondrocytes infiltrating the tumor. Of the tissues that were considered positive, only five had a 1+ expression for PRAME within the tumor cells. Of these, four were well-differentiated squamous cell carcinoma tissues, with the fifth being an adenocarcinoma. Of the poorly differentiated squamous cell carcinoma tissues tested, none were positive for PRAME. The data shows that for non-small cell lung cancer, PRAME can be a viable target for well-differentiated squamous cell carcinoma and adenocarcinoma indications.

PRAME expression was also assessed in glioblastoma tissue samples with 40% positive expression of moderate 2+ staining intensity, with the $PRAME_{276-286}$ epitope specific antibodies. PRAME was found to be expressed in all synovial sarcoma tissue samples analyzed (data not shown). PRAME was also shown to be highly expressed in liver hepatocellular carcinomas and cholangio carcinomas but not in liver combined carcinomas, as per the pathologist's assessment. Positive PRAME expression was also observed with an array of lymphomas and soft tissue sarcomas analyzed by immunohistochemistry using the $PRAME_{276-286}$ antibody.

Overall analysis of the data showed no significant expression of PRAME in normal tissues analyzed. PRAME was only expressed in normal cells infiltrating the tumors. Additionally, no expression in kidney or rectal tumors was indicated.

Example 6

Figure 2:
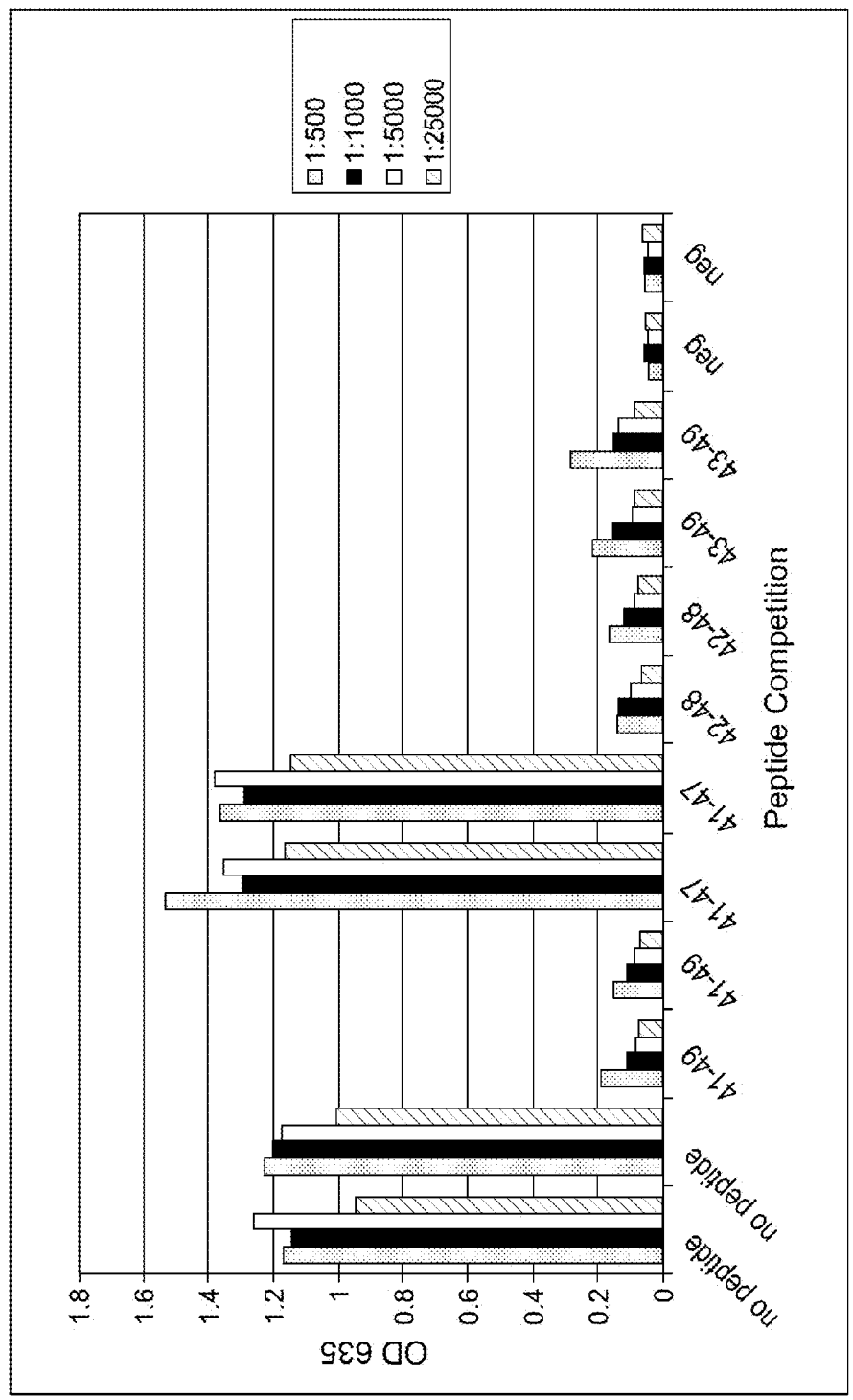
FIG. 2. Immunohistochemical staining in melanoma samples tested with an antibody specific for $PRAME_{276-286}$ epitope.

Anti-human PRAME Antibody Validation/Sensitivity Analysis in Melanoma Tissue The PRAME antibodies generated were validated for use as a diagnostic tool in immunohistochemistry assays. The results are based on a trained independent pathologist's assessment of gross tissue views. The sensitivity of mouse anti-human $PRAME_{276-286}$ antibody was evaluated by IHC on 20 human melanoma samples randomly selected from a tissue library. Formalin-fixed, paraffin-embedded tissues were used in an indirect immunohistochemistry test using the Mouse EnVision+™ detection system (DakoCytomation, Carpinteria, Calif., USA). Adequate sensitivity was demonstrated by positive nuclear and/or cytoplasmic staining of the antibody in 19 of the 20 melanoma samples tested (FIG. 2). Strong (3+) staining was observed in 65% (13/20) of the human melanoma samples. Moderate (2+) staining was observed as highest staining intensity in 25% (5/20) of the tissues tested. Weak (1+) staining was observed as highest staining intensity in 5% (1/20) of the tissues tested. No staining was observed in 5% (1/20) of the samples tested. Overall, the data correlated with previous testing in that positive cytoplasmic and nuclear staining in melanoma was observed. This was further supported by observations in the literature (Epping et al., Cancer Res. 66(22):10639-42, 2006; Tajeddine et al., Cancer Res. 65(16):7348-55, 2005; van Baren et al., Br J Haematol 102(5):1376-9, 1998), each of which is hereby incorporated by reference. The data supports the utility of the antibody for use in immunohistochemical assays.

Example 7

Peptide Competition with PRAME Antibody in Tumor Tissues

To confirm the specificity of the PRAME antibodies disclosed, a peptide competition assay was employed and various tumor tissues, (such as renal, ovarian, breast, pancreatic, prostate, colon, melanoma) analyzed by immunohistochemistry, as described elsewhere herein.

Briefly, $PRAME_{276-286}$ or $PRAME_{123-132}$ antibodies were each preincubated in the presence of an excess of peptide against which it was raised. The antibody-peptide mixture was used in parallel to the antibody alone in the immunohistochemical assay.

The data showed strong staining intensity in various tumor tissues when the antibody was used alone, but no specific staining was observed following preincubation with the PRAME peptide antigen showed 100% peptide competition with $PRAME_{276-286}$ and $PRAME_{123-132}$ antibodies, respectively). The results confirm the specificity of the $PRAME_{276-286}$ and $PRAME_{123-132}$ antibodies. Normal testes tissue was used as a positive control. No expression of PRAME antigen was noted in normal tissue with either antibody.

Example 8

Minimal Epitope Mapping of SSX-2 41-49

To determine specificity and whether the SSX-2 antibodies described herein recognize distinct or overlapping epitopes on SSX-2, minimal epitope mapping was conducted utilizing a simple ELISA capture assay with peptide competition as described in Example 3 above.

In brevity, competitive binding of the $SSX-2_{41-49}$ or $SSX-2_{120-128}$ antibody to various SSX-2 peptides was assessed with various shorter peptides used as the competitor. Each of the SSX-2 monoclonal antibodies were transferred to the pre-coated ELISA plate and incubated for 1 hour at room temperature, then discarded and rinsed five times with TBS. Horseradish peroxidase conjugated goat secondary antibody to mouse IgG was added for 1 hour at room temperature. The plates were washed and 3,3',5,5'-tetramethylbenzidine dihydrochloride (TMB) substrate (Pierce, Rockford, Ill., USA) added for colorimetric readout at 635 nm using an ELISA plate reader (Molecular Devices, Sunnyvale, Calif., USA).

Figure 3:
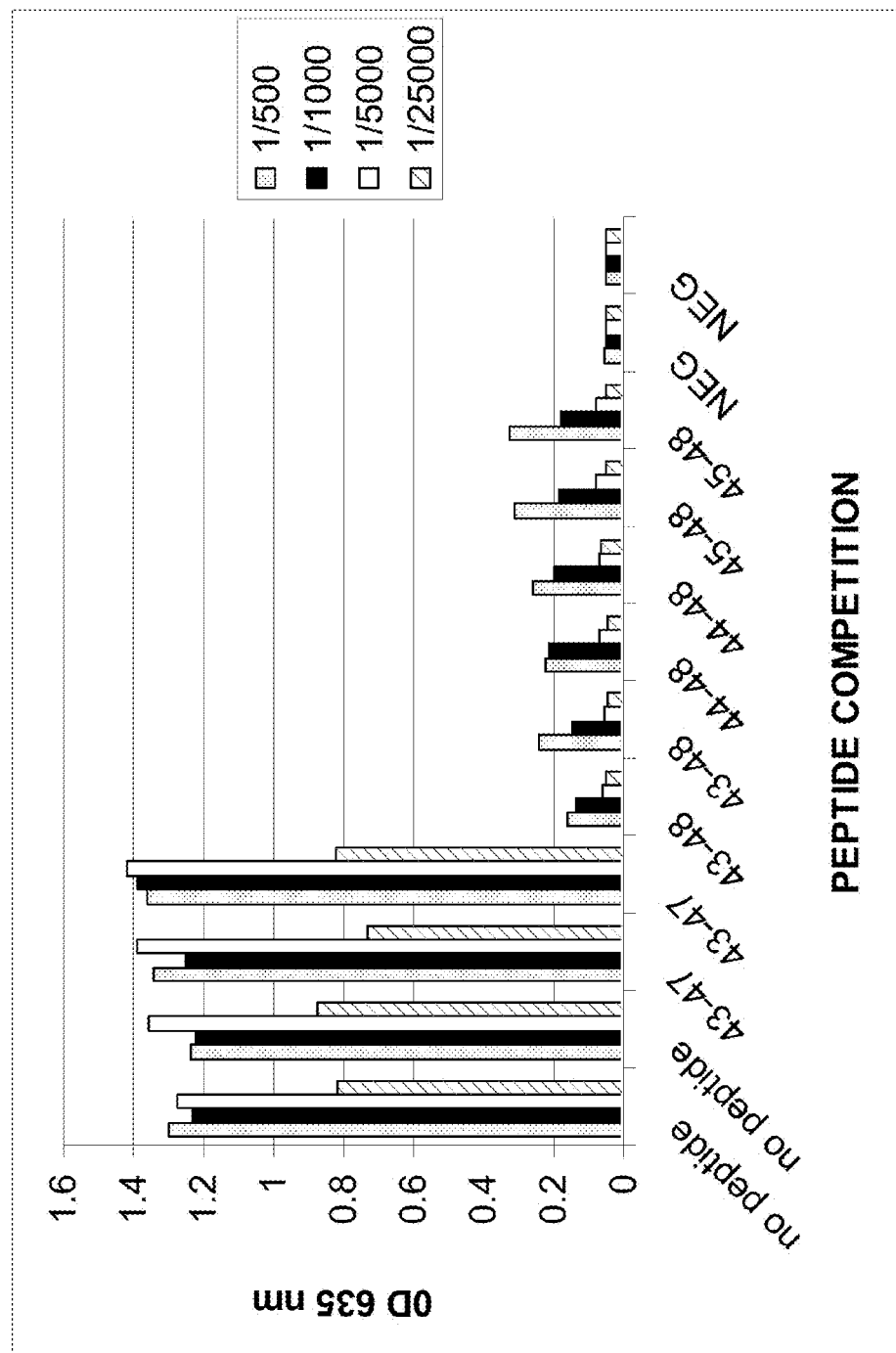
FIG. 3. Depicts minimal epitope mapping of $SSX2_{41-49}$. For each type of peptide or no peptide or negative control, serially diluted 1:500 (the first column), 1:1000 (the second column), 1:5000 (the third column) and 1:25000 (the fourth column) were analyzed.

FIG. 3 shows serial dilutions of the antibody to various SSX-2 peptides within the region of amino acid 41-49 of the SSX-2 immunogen were analyzed for competitive binding to the $SSX-2_{41-49}$ epitope. Peptides corresponding to $SSX-2_{41-47}$, $SSX-2_{42-48}$, $SSX2_{43-49}$, $SSX-2_{43-47}$, $SSX-2_{43-48}$, $SSX-2_{44-48}$, and $SSX-2_{45-48}$ were each bound to the ELISA plate and used to compete with the immunogen peptide. The antibody was serially diluted 1:500 (first column), 1:1000 (second column), 1:5000 (third column) and 1:25000 (fourth column) and analyzed by ELISA to determine whether the antibody to $SSX-2_{41-49}$ epitope recognize distinct or overlapping epitopes on SSX-2. The data shows that the minimal epitope recognition of the SSX-2$_{41-49}$ monoclonal antibody is SSX2$_{45-48}$. This also indicates the fine specificity of the exemplary SSX-2$_{41-49}$ monoclonal antibody to SSX-2$_{45-48}$ peptide. However, one of ordinary skill in the art would understand that the minimal epitope that can be recognized by an antibody may not be optimal in terms of other binding characteristics (e.g., binding affinity, and the like). BLAST protein search showed that no other known human protein shares this amino acid sequence (SSX2$_{45-48}$). The data therefore suggests that the SSX-2$_{41-49}$ antibody is specific to only SSX-2 protein.

Figure 4:
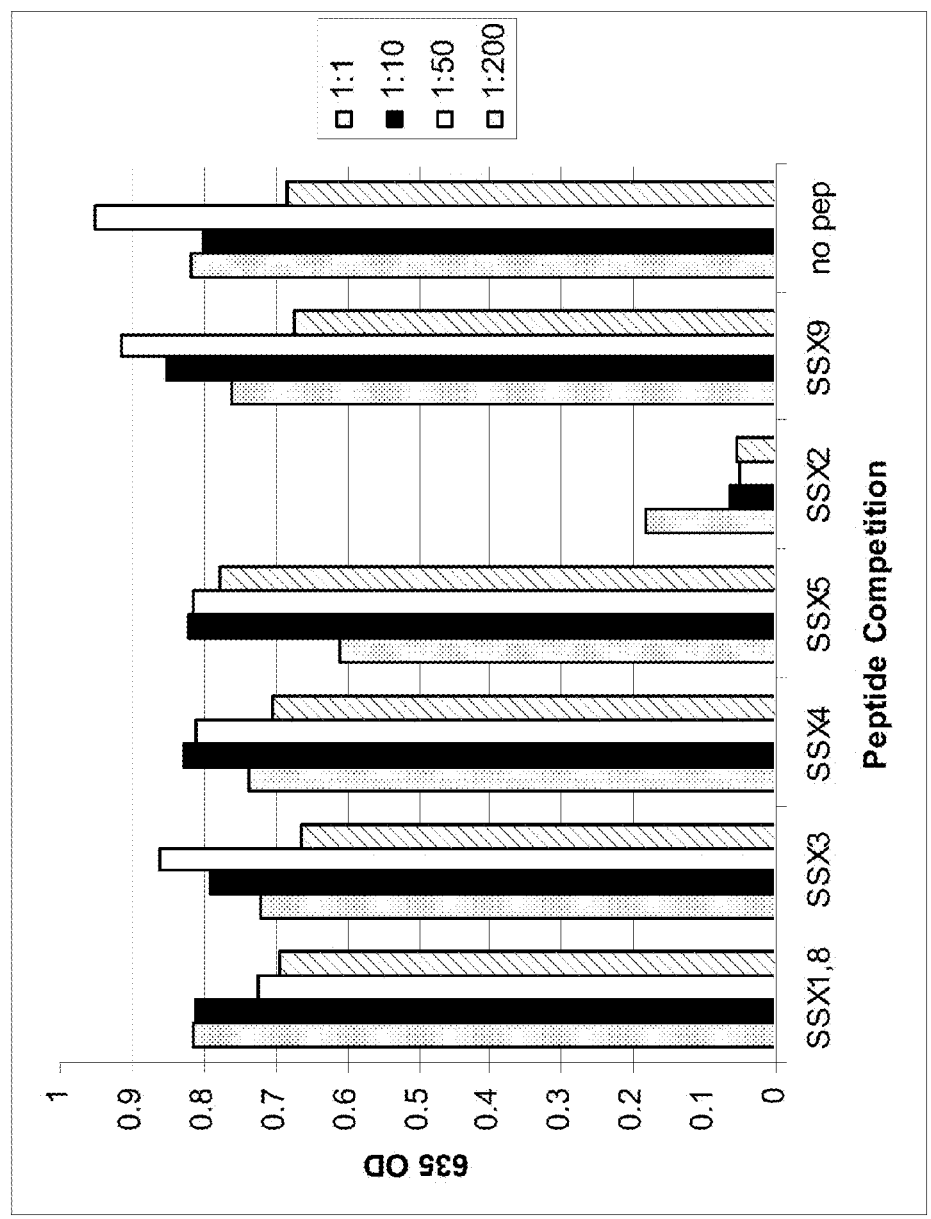
FIG. 4. Depicts that the $SSX-2_{41-49}$ monoclonal antibody does not cross react with other SSX family members. For each type of peptide of another SSX family member or no peptide, serially diluted 1:1 (the first column), 1:10 (the second column), 1:50 (the third column) and 1:200 (the fourth column) were analyzed.

The cross reactivity of SSX-2 to other members of the SSX family was tested since the peptide sequences corresponding to the antigen region are similar to the other nine members of the SSX family. The monoclonal antibody against SSX-2$_{41-49}$ showed no cross reactivity against other SSX family members (FIG. 4). The corresponding sequences are shown in Table 3.

TABLE 3

Summary of SSX family member region sequences corresponding to SSX-2$_{41-49}$

| SEQUENCES CORRESPONDING TO SSX-2$_{41-49}$ REGION | | |
|---|---|---|
| SEQ ID NO: 3 | SSX-2$_{41-49}$ | KASEKIFYV |
| SEQ ID NO: 6 | SSX-1, SSX-8: | KYSEKISYV |
| SEQ ID NO: 7 | SSX-3: | KVSEKIVYV |
| SEQ ID NO: 8 | SSX-4: | KSSEKIVYV |
| SEQ ID NO: 9 | SSX-5: | KASEKIIYV |
| SEQ ID NO: 10 | SSX-6: | KFSEKISCV |
| SEQ ID NO: 11 | SSX-7: | KSLEKISYV |
| SEQ ID NO: 12 | SSX-9: | KSSEKIIYV |

Example 9

Minimal Epitope Mapping of SSX-2$_{120-128}$

Figure 5:
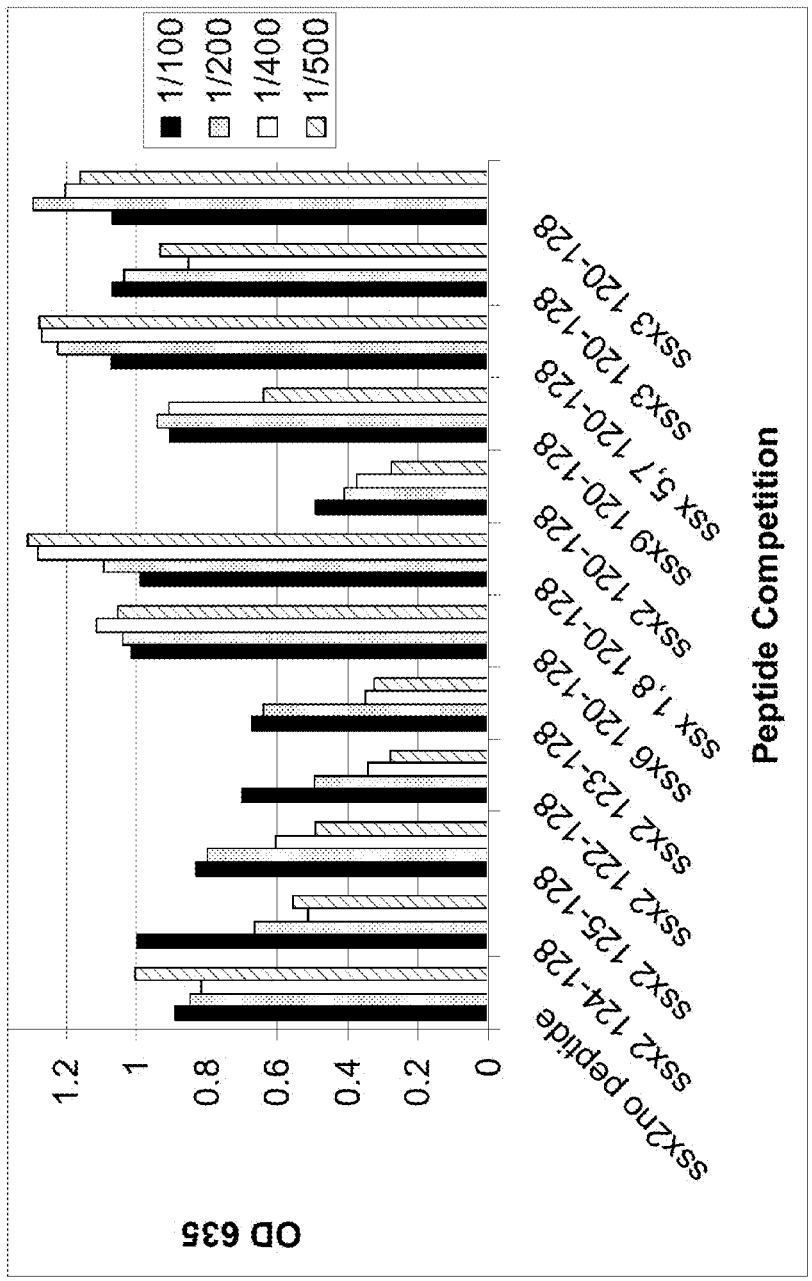
FIG. 5. Depicts minimal epitope mapping of $SSX2_{120-128}$. For each type of peptide or no peptide, serially diluted 1:100 (the first column), 1:200 (the second column), 1:400 (the third column) and 1:500 (the fourth column) were analyzed.
Figure 6:
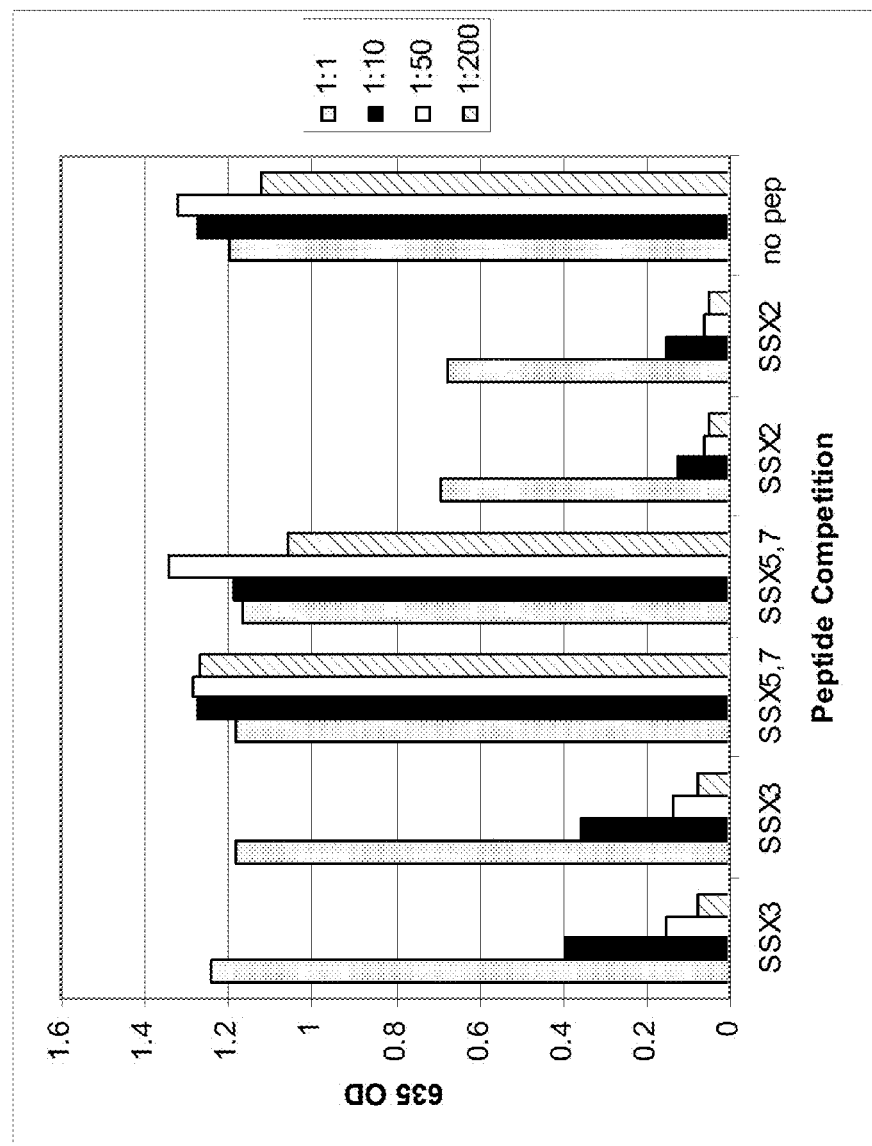
FIG. 6. Depicts the $SSX-2_{120-128}$ monoclonal antibody cross reactivity with other SSX family members. For each type of peptide of another SSX family member or no peptide, serially diluted 1:1 (the first column), 1:10 (the second column), 1:50 (the third column) and 1:200 (the fourth column) were analyzed.

To determine whether the antibody to SSX-2$_{120-128}$ epitope recognize distinct or overlapping epitopes on SSX-2. Peptides within the region of amino acid 120 to 128 were tested as competitors as described in Example 8, above. Peptides corresponding to SSX-2$_{124-128}$; WC-2$_{125-128}$; SSX-2$_{122-128}$; SSX-2$_{123-128}$ were bound to the plate and antibody was serially diluted 1:100 (first column), 1:200 (second column), 1:400 (third column) and 1:500 (fourth column) and analyzed by ELISA and used to compete with the immunogen peptide to determine whether the antibody to SSX-2$_{120-128}$ epitope recognize distinct or overlapping epitopes on SSX-2 (FIG. 5). The data shows that the minimal epitope recognition of the SSX-2$_{120-128}$ monoclonal antibody is SSX-2$_{123-128}$. This also indicates the fine specificity of the exemplary SSX-2$_{120-128}$ monoclonal antibody to SSX-2$_{123-128}$ peptide. However, one of ordinary skill in the art would understand that the minimal epitope that can be recognized by an antibody may not be optimal in terms of other binding characteristics (e.g., binding affinity, and the like). BLAST protein search showed that no other known human protein shares this amino acid sequence (SSX2$_{123-128}$). The data therefore suggests that the SSX-2$_{120-128}$ antibody is specific to only SSX-2 protein. In addition, other peptides corresponding to various SSX family proteins: SSX-6$_{120-128}$; SSX-1,8$_{120-128}$; SSX-9$_{120-128}$; SSX-5,7$_{120-128}$; and SSX-3$_{120-128}$ were tested to determine the cross-reactivity with the SSX-2$_{120-128}$ epitope. The data showed that SSX-2$_{120-128}$ is partially cross reactive with peptides corresponding to other SSX family members, such as SSX-3 (FIG. 6). It is noted that SSX-3 is only expressed in sarcomas, or cancer of connective or supportive tissue (these types of tissue include bone, cartilage, fat, muscle, and blood vessels), not in the cancerous cells of interest.

TABLE 4

Summary of SSX family member region sequences corresponding to SSX-2$_{120-128}$

| SEQUENCES CORRESPONDING TO SSX-2$_{120-128}$ REGION | | |
|---|---|---|
| SEQ ID NO: 4 | SSX2$_{120-128}$: | GNDSEEVPE |
| SEQ ID NO: 13 | SSX-1, SSX-8: | GNDSKGVSE |
| SEQ ID NO: 14 | SSX-3: | GNVSKEVPE |
| SEQ ID NO: 15 | SSX-4: | GNGLKEVPE |
| SEQ ID NO: 16 | SSX-5, SSX-7: | GNDSKGVPE |
| SEQ ID NO: 17 | SSX-6: | GSDSKGVPE |
| SEQ ID NO: 18 | SSX-9: | GNDSKEVPE |

Example 10

Determining Antibody Isotype of SSX-2 Antibodies

Using a similar protocol as the ELISA capture assay described above in Example 3, ELISA plates were coated with antibody to various isotypes, such as, IgG1, IgG2, IgG3, IgG4, IgM, and subtypes thereof. An aliquot (1 microgram per milliliter) of the antibody clone to the SSX-2$_{41-49}$ epitope or the antibody to SSX-2$_{120-128}$ epitope (1 microgram per milliliter) in PBS+1% BSA was added in each well and incubated at room temperature.

After the supernatant was discarded and the plate rinsed with TBS, HRP-labeled rat anti-mouse 1 g mAb was used as a secondary antibody. A colorimetric assay was used to determine the isotype of the SSX-2$_{41-49}$ and SSX-2$_{120-128}$ antibodies. Based on the data obtained, the antibody raised against SSX-2$_{41-49}$ was found to be an IgG2b antibody and the antibody raised against SSX-2$_{120-128}$ was found to be an IgG1 antibody.

Example 11

Detection of SSX-2 Expression in Tumor Tissues and Cells

The SSX-2 monoclonal antibody specific to the SSX-2$_{41-49}$ epitope and the SSX-2$_{120-128}$ epitope as described above, were used to analyze tissue samples of various types of cancers, (for example, breast, colorectal, ovarian, melanoma, pancreatic, prostate, renal, and synovial sarcoma), by immunohistochemistry (as described in Example 1 and 3 above), and determine the expression frequency of the SSX-2 tumor-associated antigen (TAA) expression in various types of cancers. Expression of SSX-2 was also compared to normal adult tissues for each of the tumor tissues analyzed. Tissues from normal testis, (being positive for cancer-testis antigens), was used as a positive control.

By immunohistochemical staining with an antibody specific for SSX-2$_{41-49}$ epitope, the expression profile of SSX-2 tumour associated antigen in primary tumors was assessed, as exemplified in Table 5. SSX-2 was expressed in over 50% of the samples in all of the tumors indicated, by QRT-PCR analysis of both mRNA expression and IHC staining in parallel, except for renal cancer in which 27% of the samples showed positive expression by IHC.

The percentage of various cell types of tumor tissue specimens expressing SSX-2 is shown in Table 6. Cell types indicated in Table 6 are represented as follows Norm—normal normal cells within the tumor specimen and other cell types infiltrating the tumor; EC—endothelial cells; SM—smooth muscle; Fibro—fibroblast; Stroma; LC—lymphocyte cells; and Nerve cells. The data show no staining of cell type representative of the nerve, stroma or smooth muscle by antibodies of the disclosure, in any of the cancers tested.

TABLE 5

| Cancers | SSX-2 Expression QRT-PCR | SSX-2 Expression IHC |
|---|---|---|
| Ovarian | 18.4% (38 samples) | 61% (33 samples) |
| Breast | 13.3% (30 samples) | 57% (28 samples) |
| Prostate | 6.5% (31 samples) | 87% (30 samples) |
| Colon | 7.9% (38 samples) | 63% (43 samples) |
| Renal | 5.6% (18 samples) | 27% (26 samples) |
| Pancreas | 6.7% (15 samples) | 55% (22 samples) |
| Melanoma | 25% (12 samples) | 69% (35 samples) |

TABLE 6

| | SSX-2 % Staining of other cell types | | | | | |
|---|---|---|---|---|---|---|
| Cancer | Norm | EC | SM | Fibro | Stroma | LC | Nerve |
| Pancreas | 27 | 31 | 0 | 17 | 0 | 13 | 0 |
| Renal | 8 | 4 | 0 | 4 | 0 | 12 | 0 |
| Melanoma | 8 | 57 | 0 | 8 | 0 | 49 | 0 |
| Ovarian | 0 | 36 | 0 | 54 | 0 | 55 | 0 |
| Breast | 3 | 37 | 0 | 37 | 3 | 53 | 0 |
| Prostate | 57 | 30 | 0 | 56 | 0 | 35 | 4 |
| Colorectal | 5 | 21 | 0 | 14 | 0 | 47 | 0 |

Example 12

Peptide Competition with SSX-2 Antibody in Tumor Tissues

To confirm the specificity of the SSX-2 antibodies disclosed, a peptide competition assay was employed and various tumor tissues, (for example, breast, colorectal, ovarian, melanoma, pancreatic, prostate, renal, and synovial sarcoma), analyzed by immunohistochemistry, as described elsewhere herein.

Briefly, SSX-2$_{41-49}$ or SSX-2$_{120-128}$ antibodies were each preincubated in the presence of an excess of peptide against which it was raised. The antibody-peptide mixture was used in parallel to the antibody alone in the immunohistochemical assay.

The data showed strong staining intensity in various tumor tissues when the SSX-2$_{41-49}$ or SSX-2$_{120-128}$ antibody was used alone. No specific staining was observed following preincubation with the SSX-2 peptide antigen. The results confirm the specificity of the SSX-2$_{41-49}$ and SSX-2$_{120-128}$ antibodies. Additionally, the data showed that although SSX-2$_{120-128}$ is partially cross reactive with other SSX family members, such as SSX-3 as discussed in Example 9 above; SSX-2$_{120-128}$ showed. 100% peptide competition on tumor tested. This is most likely attributed to SSX3 being minimally expressed in these tumors. Normal testes tissue was used as a positive control.

The various methods and techniques described above provide a number of ways to practice that disclosed. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as can be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some can be specifically included and others specifically excluded in diverse embodiments.

Although the invention has been disclosed in the context of certain embodiments and examples, it will be understood by those skilled in the art that the disclosure extends beyond the specifically disclosed embodiments to other alternative embodiments and/or uses and modifications and equivalents thereof.

Many variations and alternative elements of the disclosure have been disclosed. Still further variations and alternate elements will be apparent to one of skill in the art. Among these variations, without limitation, are the specific number of antigens in a screening panel or targeted by a therapeutic product, the type of antigen, the type of cancer, and the particular antigen(s) specified. Various embodiments of the disclosure can specifically include or exclude any of these variations or elements.

In some embodiments, the numbers expressing quantities of ingredients, properties such as molecular weight, reaction conditions, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclosure can contain certain errors necessarily resulting from the standard deviation found in their respective testing measurements.

In some embodiments, the terms "a" and "an" and "the" and similar referents used in the context of describing a particular embodiment of the disclosure (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context The use of any and all examples, or exemplary language (e.g. "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Particular embodiments of this disclosure are described herein, including the best mode known to the inventors in the practice of the disclosure. Variations on those embodiments will become apparent to those of ordinary skill in the art upon reading the foregoing description. It is contemplated that skilled artisans can employ such variations as appropriate, and the disclosure can be practiced otherwise than specifically described herein. Accordingly, many embodiments of this disclosure include all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above cited references and printed publications is herein individually incorporated by reference in its entirety to the extent that their content does not conflict with the disclosure directly presented herein.

```
                                              (SEQ ID NO: 1)
                        PRAME 123-132-DLRKNSHQDF (SEQ ID NO: 2)
                        Prame 276-286-ISPEKEEQYIA (SEQ ID NO: 3)
                        SSX2 41-49-KASEKIFYV (SEQ ID NO: 4)
                        SSX2 120-128-GNDSEEVPE
```

What is claimed is:

1. An antibody, or antigen-binding fragment thereof, directed against PRAME antigen that binds $PRAME_{123-132}$ (SEQ ID NO:1) or $PRAME_{276-286}$ (SEQ ID NO:2).

2. The antibody of claim 1, wherein the antibody is a monoclonal antibody.

3. The antibody of claim 2, wherein the antibody is a murine, chimeric, humanized, or human antibody.

4. The antibody of claim 3, further linked to a label.

5. A method of detecting expression of tumor associated antigen PRAME in a biological sample, the method comprising
   contacting the biological sample with an antibody of anyone of the preceding claims, and
   detecting antibody bound to antigen in the sample, thereby detecting the expression of the tumor associated antigen.

6. The method of claim 5, further comprising obtaining the biological sample from a subject.

7. The method of claim 5, wherein the antibody is specific to SEQ ID NO:1.

8. The method of claim 5, wherein the antibody is specific to SEQ ID NO:2.

9. The method of claim 6, wherein the subject has cancer, and wherein the cancer is selected from the group consisting of melanoma, kidney, breast, pancreas, prostate, colorectal, liver, ovarian, non small cell lung cancer, glioblastoma, ocular melanoma, hormone sensitive and hormone refractory prostate cancer, renal cell carcinoma, esophageal, endometrial cancer, uterine cancer, lymphoma, soft tissue sarcoma, multiple myeloma, gallbladder cancer, thyroid and mesothelioma.

10. The method of claim 5, wherein the biological sample comprises a biopsy specimen, a tissue, a cell, blood, ascites, pleural fluid, or a soluble protein.

11. The method of claim 5, wherein expression of PRAME is detected by immunofluorescence microscopy, immunocytochemistry, immunohistochemistry, ELISA, FACS analysis or immunoprecipitation.

12. A plasmid operably encoding the antibody, or an antigen binding fragment thereof, of claim 1.

13. A hybridoma that produces a monoclonal antibody of claim 2.

14. A kit comprising the antibody, or antigen binding fragment thereof, of claim 1.

15. The antibody, or antigen-binding fragment thereof, of claim 1, wherein the antibody, or antigen-binding fragment thereof, also binds a fragment of PRAME.

* * * * *

SEQUENCE LISTING

```
<160> NUMBER OF SEQ ID NOS: 18

<210> SEQ ID NO 1
<211> LENGTH: 10
<212> TYPE: PRT
<213> ORGANISM: Homo Sapiens

<400> SEQUENCE: 1

Asp Leu Arg Lys Asn Ser His Gln Asp Phe
1               5                   10

<210> SEQ ID NO 2
<211> LENGTH: 11
<212> TYPE: PRT
<213> ORGANISM: Homo Sapiens

<400> SEQUENCE: 2

Ile Ser Pro Glu Lys Glu Glu Gln Tyr Ile Ala
1               5                   10

<210> SEQ ID NO 3
<211> LENGTH: 9
<212> TYPE: PRT
<213> ORGANISM: Homo Sapiens

<400> SEQUENCE: 3

Lys Ala Ser Glu Lys Ile Phe Tyr Val
1               5

<210> SEQ ID NO 4
<211> LENGTH: 9
<212> TYPE: PRT
<213> ORGANISM: Homo Sapiens
```

```
<400> SEQUENCE: 4

Gly Asn Asp Ser Glu Glu Val Pro Glu
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 5

Ile Ser Pro Glu Lys Glu Glu Gln Tyr Ile Cys
1               5                   10

<210> SEQ ID NO 6
<211> LENGTH: 9
<212> TYPE: PRT
<213> ORGANISM: Homo Sapiens

<400> SEQUENCE: 6

Lys Tyr Ser Glu Lys Ile Ser Tyr Val
1               5

<210> SEQ ID NO 7
<211> LENGTH: 9
<212> TYPE: PRT
<213> ORGANISM: Homo Sapiens

<400> SEQUENCE: 7

Lys Val Ser Glu Lys Ile Val Tyr Val
1               5

<210> SEQ ID NO 8
<211> LENGTH: 9
<212> TYPE: PRT
<213> ORGANISM: Homo Sapiens

<400> SEQUENCE: 8

Lys Ser Ser Glu Lys Ile Val Tyr Val
1               5

<210> SEQ ID NO 9
<211> LENGTH: 9
<212> TYPE: PRT
<213> ORGANISM: Homo Sapiens

<400> SEQUENCE: 9

Lys Ala Ser Glu Lys Ile Ile Tyr Val
1               5

<210> SEQ ID NO 10
<211> LENGTH: 9
<212> TYPE: PRT
<213> ORGANISM: Homo Sapiens

<400> SEQUENCE: 10

Lys Phe Ser Glu Lys Ile Ser Cys Val
1               5

<210> SEQ ID NO 11
<211> LENGTH: 9
<212> TYPE: PRT
<213> ORGANISM: Homo Sapiens
```

```
<400> SEQUENCE: 11

Lys Ser Leu Glu Lys Ile Ser Tyr Val
1               5

<210> SEQ ID NO 12
<211> LENGTH: 9
<212> TYPE: PRT
<213> ORGANISM: Homo Sapiens

<400> SEQUENCE: 12

Lys Ser Ser Glu Lys Ile Ile Tyr Val
1               5

<210> SEQ ID NO 13
<211> LENGTH: 9
<212> TYPE: PRT
<213> ORGANISM: Homo Sapiens

<400> SEQUENCE: 13

Gly Asn Asp Ser Lys Gly Val Ser Glu
1               5

<210> SEQ ID NO 14
<211> LENGTH: 9
<212> TYPE: PRT
<213> ORGANISM: Homo Sapiens

<400> SEQUENCE: 14

Gly Asn Val Ser Lys Glu Val Pro Glu
1               5

<210> SEQ ID NO 15
<211> LENGTH: 9
<212> TYPE: PRT
<213> ORGANISM: Homo Sapiens

<400> SEQUENCE: 15

Gly Asn Gly Leu Lys Glu Val Pro Glu
1               5

<210> SEQ ID NO 16
<211> LENGTH: 9
<212> TYPE: PRT
<213> ORGANISM: Homo Sapiens

<400> SEQUENCE: 16

Gly Asn Asp Ser Lys Gly Val Pro Glu
1               5

<210> SEQ ID NO 17
<211> LENGTH: 9
<212> TYPE: PRT
<213> ORGANISM: Homo Sapiens

<400> SEQUENCE: 17

Gly Ser Asp Ser Lys Gly Val Pro Glu
1               5

<210> SEQ ID NO 18
<211> LENGTH: 9
<212> TYPE: PRT
<213> ORGANISM: Homo Sapiens
```

```
<400> SEQUENCE: 18

Gly Asn Asp Ser Lys Glu Val Pro Glu
 1               5
```